US009931131B2

(12) United States Patent
Dumbauld et al.

(10) Patent No.: US 9,931,131 B2
(45) Date of Patent: Apr. 3, 2018

(54) IN VIVO ATTACHABLE AND DETACHABLE END EFFECTOR ASSEMBLY AND LAPAROSCOPIC SURGICAL INSTRUMENT AND METHODS THEREFOR

(71) Applicant: COVIDIEN LP, Mansfield, MA (US)

(72) Inventors: Patrick L. Dumbauld, Lyons, CO (US); Edward Cosgriff, Denver, CO (US)

(73) Assignee: COVIDIEN LP, Mansfield, MA (US)

( * ) Notice: Subject to any disclaimer, the term of this patent is extended or adjusted under 35 U.S.C. 154(b) by 319 days.

(21) Appl. No.: 14/708,950

(22) Filed: May 11, 2015

(65) Prior Publication Data
US 2015/0245847 A1 Sep. 3, 2015

Related U.S. Application Data

(63) Continuation of application No. 13/415,639, filed on Mar. 8, 2012, now Pat. No. 9,028,493, which is a
(Continued)

(51) Int. Cl.
A61B 17/29 (2006.01)
A61B 17/28 (2006.01)
(Continued)

(52) U.S. Cl.
CPC ...... *A61B 17/2812* (2013.01); *A61B 18/1445* (2013.01); *A61B 18/1482* (2013.01);
(Continued)

(58) Field of Classification Search
CPC ............ A61B 18/1445; A61B 18/1482; A61B 2018/00601; A61B 2018/0063;
(Continued)

(56) References Cited

U.S. PATENT DOCUMENTS 371,664 A 10/1887 Brannan et al.
702,472 A 6/1902 Pignolet
(Continued)

FOREIGN PATENT DOCUMENTS

CA 2104423 A1 2/1994
CA 2520413 A1 3/2007
(Continued)

OTHER PUBLICATIONS

Michael Choti, "Abdominoperineal Resection with the LigaSure Vessel Sealing System and LigaSure Atlas 20 cm Open Instrument"; Innovations That Work, Jun. 2003.
(Continued)

*Primary Examiner* — Michael Peffley

(57) ABSTRACT

A method of performing surgery includes the steps of providing a forceps having a housing including a shaft that extends therefrom and at least one handle moveable relative to the housing and providing an end effector assembly configured to selectively engage a distal end of the shaft. The method also includes the steps of inserting the forceps through a first opening formed in a body; inserting the end effector assembly through a second opening formed in the body; engaging the end effector assembly with the distal end of the shaft in vivo; and actuating the end effector assembly by moving the handle relative to the housing. The method may also include the steps of providing a coupling at the distal end of the shaft, and engaging, via the coupling, the distal end of the shaft with the end effector assembly.

12 Claims, 10 Drawing Sheets

Related U.S. Application Data continuation of application No. 12/562,281, filed on Sep. 18, 2009, now Pat. No. 8,133,254.

(51) Int. Cl.
*A61B 18/14* (2006.01)
*A61B 17/00* (2006.01)
*A61B 18/00* (2006.01)

(52) U.S. Cl.
CPC .............. *A61B 2017/00473* (2013.01); *A61B 2017/2931* (2013.01); *A61B 2017/2945* (2013.01); *A61B 2017/2946* (2013.01); *A61B 2017/2947* (2013.01); *A61B 2018/0063* (2013.01); *A61B 2018/00601* (2013.01); *A61B 2018/1412* (2013.01); *A61B 2018/1432* (2013.01); *A61B 2018/1455* (2013.01)

(58) Field of Classification Search
CPC .... A61B 2018/1412; A61B 2018/1432; A61B 2018/1455; A61B 17/28; A61B 17/2812; A61B 17/29; A61B 2017/2931; A61B 2017/294; A61B 2017/2945; A61B 2017/2946; A61B 2017/2947; A61B 2017/00473
See application file for complete search history.

(56) References Cited

U.S. PATENT DOCUMENTS

| | | |
|---|---|---|
| 728,883 A | 5/1903 | Downes |
| 1,586,645 A | 6/1926 | Bierman |
| 1,813,902 A | 7/1931 | Bovie |
| 1,822,330 A | 9/1931 | Ainslie |
| 1,852,542 A | 4/1932 | Sovatkin |
| 1,908,201 A | 5/1933 | Welch et al. |
| 1,918,889 A | 7/1933 | Bacon |
| 2,002,594 A | 5/1935 | Wappler et al. |
| 2,011,169 A | 8/1935 | Wappler |
| 2,031,682 A | 2/1936 | Wappler et al. |
| 2,054,149 A | 9/1936 | Wappler |
| 2,113,246 A | 4/1938 | Wappler |
| 2,141,936 A | 12/1938 | Schmitt |
| 2,176,479 A | 10/1939 | Willis |
| 2,245,030 A | 6/1941 | Gottesfeld et al. |
| 2,279,753 A | 4/1942 | Knopp |
| 2,305,156 A | 12/1942 | Grubel |
| 2,327,353 A | 8/1943 | Karle |
| 2,632,661 A | 3/1953 | Cristofv |
| 2,668,538 A | 2/1954 | Baker |
| 2,796,065 A | 6/1957 | Kapp |
| 2,824,915 A | 2/1958 | Buturuga |
| 3,073,311 A | 1/1963 | Tibbs et al. |
| 3,100,489 A | 8/1963 | Bagley |
| 3,204,807 A | 9/1965 | Ramsing |
| 3,372,288 A | 3/1968 | Wigington |
| 3,459,187 A | 8/1969 | Pallotta |
| 3,561,448 A | 2/1971 | Peternel |
| 3,643,663 A | 2/1972 | Sutter |
| 3,648,001 A | 3/1972 | Anderson et al. |
| 3,651,811 A | 3/1972 | Hildebrandt et al. |
| 3,678,229 A | 7/1972 | Osika |
| 3,720,896 A | 3/1973 | Beierlein |
| 3,763,726 A | 10/1973 | Hildebrand |
| 3,779,918 A | 12/1973 | Ikeda et al. |
| 3,798,688 A | 3/1974 | Wasson |
| 3,801,766 A | 4/1974 | Morrison, Jr. |
| 3,839,614 A | 10/1974 | Saganowski et al. |
| 3,862,630 A | 1/1975 | Balamuth |
| 3,863,339 A | 2/1975 | Reaney et al. |
| 3,866,610 A | 2/1975 | Kletschka |
| 3,875,945 A | 4/1975 | Friedman |
| 3,897,786 A | 8/1975 | Garnett et al. |
| 3,911,766 A | 10/1975 | Fridolph et al. |
| 3,920,021 A | 11/1975 | Hiltebrandt |
| 3,921,641 A | 11/1975 | Hulka |
| 3,938,527 A | 2/1976 | Rioux et al. |
| 3,952,749 A | 4/1976 | Fridolph et al. |
| 3,970,088 A | 7/1976 | Morrison |
| 3,987,795 A | 10/1976 | Morrison |
| 4,005,714 A | 2/1977 | Hiltebrandt |
| 4,016,881 A | 4/1977 | Rioux et al. |
| 4,031,898 A | 6/1977 | Hiltebrandt et al. |
| 4,041,952 A | 8/1977 | Morrison, Jr. et al. |
| 4,043,342 A | 8/1977 | Morrison, Jr. |
| 4,074,718 A | 2/1978 | Morrison, Jr. |
| 4,076,028 A | 2/1978 | Simmons |
| 4,080,820 A | 3/1978 | Allen |
| 4,088,134 A | 5/1978 | Mazzariello |
| 4,102,471 A | 7/1978 | Lore et al. |
| D249,549 S | 9/1978 | Pike |
| 4,112,950 A | 9/1978 | Pike |
| 4,127,222 A | 11/1978 | Adams |
| 4,128,099 A | 12/1978 | Bauer |
| 4,165,746 A | 8/1979 | Burgin |
| 4,187,420 A | 2/1980 | Piber |
| 4,200,104 A | 4/1980 | Harris |
| 4,200,105 A | 4/1980 | Gonser |
| 4,233,734 A | 11/1980 | Bies |
| 4,236,470 A | 12/1980 | Stenson |
| 4,274,413 A | 6/1981 | Hahn et al. |
| 4,300,564 A | 11/1981 | Furihata |
| 4,306,561 A | 12/1981 | de Medinaceli |
| 4,311,145 A | 1/1982 | Esty et al. |
| D263,020 S | 2/1982 | Rau, III |
| 4,315,510 A | 2/1982 | Kihn |
| 4,363,944 A | 12/1982 | Poirier |
| 4,370,980 A | 2/1983 | Lottick |
| 4,375,218 A | 3/1983 | DiGeronimo |
| 4,394,552 A | 7/1983 | Schlosser |
| 4,416,276 A | 11/1983 | Newton et al. |
| 4,418,692 A | 12/1983 | Guay |
| 4,443,935 A | 4/1984 | Zamba et al. |
| 4,452,246 A | 6/1984 | Bader et al. |
| 4,470,786 A | 9/1984 | Sano et al. |
| 4,492,231 A | 1/1985 | Auth |
| 4,493,320 A | 1/1985 | Treat |
| 4,503,855 A | 3/1985 | Maslanka |
| 4,506,669 A | 3/1985 | Blake |
| 4,509,518 A | 4/1985 | McGarry et al. |
| 4,513,271 A | 4/1985 | Reisem |
| 4,535,773 A | 8/1985 | Yoon |
| 4,552,143 A | 11/1985 | Lottick |
| 4,574,804 A | 3/1986 | Kurwa |
| 4,597,379 A | 7/1986 | Kihn et al. |
| 4,600,007 A | 7/1986 | Lahodny et al. |
| 4,619,258 A | 10/1986 | Pool |
| 4,624,254 A | 11/1986 | McGarry et al. |
| 4,644,950 A | 2/1987 | Valli |
| 4,655,215 A | 4/1987 | Pike |
| 4,655,216 A | 4/1987 | Tischer |
| 4,657,016 A | 4/1987 | Garito et al. |
| 4,662,372 A | 5/1987 | Sharkany et al. |
| 4,671,274 A | 6/1987 | Sorochenko |
| 4,674,499 A | 6/1987 | Pao |
| 4,685,459 A | 8/1987 | Koch et al. |
| 4,733,662 A | 3/1988 | DeSatnick et al. |
| D295,893 S | 5/1988 | Sharkany et al. |
| D295,894 S | 5/1988 | Sharkany et al. |
| 4,753,235 A | 6/1988 | Hasson |
| 4,754,892 A | 7/1988 | Retief |
| 4,763,669 A | 8/1988 | Jaeger |
| D298,353 S | 11/1988 | Manno |
| 4,781,175 A | 11/1988 | McGreevy et al. |
| D299,413 S | 1/1989 | DeCarolis |
| 4,805,616 A | 2/1989 | Pao |
| 4,827,927 A | 5/1989 | Newton |
| 4,827,929 A | 5/1989 | Hodge |
| 4,829,313 A | 5/1989 | Taggart |
| 4,846,171 A | 7/1989 | Kauphusman et al. |
| 4,887,612 A | 12/1989 | Esser et al. |
| 4,890,610 A | 1/1990 | Kirwan, Sr. et al. |
| 4,938,761 A | 7/1990 | Ensslin |

(56) References Cited

U.S. PATENT DOCUMENTS

| | | |
|---|---|---|
| 4,947,009 A | 8/1990 | Osika et al. |
| 4,973,801 A | 11/1990 | Frick et al. |
| 4,985,030 A | 1/1991 | Melzer et al. |
| 5,007,908 A | 4/1991 | Rydell |
| 5,026,370 A | 6/1991 | Lottick |
| 5,026,371 A | 6/1991 | Rydell et al. |
| 5,035,695 A | 7/1991 | Weber, Jr. et al. |
| 5,037,433 A | 8/1991 | Wilk et al. |
| 5,042,707 A | 8/1991 | Taheri |
| 5,047,046 A | 9/1991 | Bodoia |
| 5,052,402 A | 10/1991 | Bencini et al. |
| 5,078,716 A | 1/1992 | Doll |
| 5,084,057 A | 1/1992 | Green et al. |
| 5,085,659 A | 2/1992 | Rydell |
| 5,099,840 A | 3/1992 | Goble et al. |
| 5,100,430 A | 3/1992 | Avellanet et al. |
| 5,108,392 A | 4/1992 | Spingler |
| 5,112,343 A | 5/1992 | Thornton |
| 5,116,332 A | 5/1992 | Lottick |
| 5,122,139 A | 6/1992 | Sutter |
| 5,144,323 A | 9/1992 | Yonkers |
| 5,147,357 A | 9/1992 | Rose et al. |
| 5,151,102 A | 9/1992 | Kamiyama et al. |
| 5,151,978 A | 9/1992 | Bronikowski et al. |
| 5,158,561 A | 10/1992 | Rydell et al. |
| 5,169,396 A | 12/1992 | Dowlatshahi et al. |
| 5,176,695 A | 1/1993 | Dulebohn |
| 5,190,541 A | 3/1993 | Abele et al. |
| 5,196,009 A | 3/1993 | Kirwan, Jr. |
| 5,197,964 A | 3/1993 | Parins |
| 5,209,747 A | 5/1993 | Knoepfler |
| 5,211,655 A | 5/1993 | Hasson |
| 5,215,101 A | 6/1993 | Jacobs et al. |
| 5,217,457 A | 6/1993 | Delahuerga et al. |
| 5,217,458 A | 6/1993 | Parins |
| 5,217,460 A | 6/1993 | Knoepfler |
| 5,219,354 A | 6/1993 | Choudhury et al. |
| 5,244,462 A | 9/1993 | Delahuerga et al. |
| 5,250,047 A | 10/1993 | Rydell |
| 5,250,056 A | 10/1993 | Hasson |
| 5,250,063 A | 10/1993 | Abidin et al. |
| 5,254,129 A | 10/1993 | Alexander |
| 5,258,001 A | 11/1993 | Corman |
| 5,258,006 A | 11/1993 | Rydell et al. |
| 5,261,918 A | 11/1993 | Phillips et al. |
| 5,267,998 A | 12/1993 | Hagen |
| 5,269,780 A | 12/1993 | Roos |
| 5,269,804 A | 12/1993 | Bales et al. |
| D343,453 S | 1/1994 | Noda |
| 5,275,615 A | 1/1994 | Rose |
| 5,277,201 A | 1/1994 | Stern |
| 5,281,220 A | 1/1994 | Blake, III |
| 5,282,799 A | 2/1994 | Rydell |
| 5,282,800 A | 2/1994 | Foshee et al. |
| 5,282,826 A | 2/1994 | Quadri |
| 5,290,286 A | 3/1994 | Parins |
| 5,290,287 A | 3/1994 | Boebel et al. |
| 5,300,082 A | 4/1994 | Sharpe et al. |
| 5,304,203 A | 4/1994 | El-Mallawany et al. |
| 5,308,353 A | 5/1994 | Beurrier |
| 5,308,357 A | 5/1994 | Lichtman |
| 5,312,433 A | 5/1994 | Boebel et al. |
| 5,313,027 A | 5/1994 | Inoue et al. |
| 5,314,445 A | 5/1994 | Heidmueller et al. |
| 5,314,463 A | 5/1994 | Camps et al. |
| 5,318,589 A | 6/1994 | Lichtman |
| 5,324,289 A | 6/1994 | Eggers |
| D348,930 S | 7/1994 | Olson |
| 5,326,806 A | 7/1994 | Yokoshima et al. |
| 5,330,471 A | 7/1994 | Eggers |
| 5,330,502 A | 7/1994 | Hassler et al. |
| D349,341 S | 8/1994 | Lichtman et al. |
| 5,334,166 A | 8/1994 | Palestrant |
| 5,334,183 A | 8/1994 | Wuchinich |
| 5,334,215 A | 8/1994 | Chen |
| 5,336,220 A | 8/1994 | Ryan et al. |
| 5,336,221 A | 8/1994 | Anderson |
| 5,342,359 A | 8/1994 | Rydell |
| 5,342,381 A | 8/1994 | Tidemand |
| 5,342,393 A | 8/1994 | Stack |
| 5,344,424 A | 9/1994 | Roberts et al. |
| 5,350,391 A | 9/1994 | Iacovelli |
| 5,352,222 A | 10/1994 | Rydell |
| 5,354,271 A | 10/1994 | Voda |
| 5,356,408 A | 10/1994 | Rydell |
| 5,359,993 A | 11/1994 | Slater et al. |
| 5,366,477 A | 11/1994 | LeMarie, III et al. |
| 5,367,250 A | 11/1994 | Whisenand |
| 5,368,600 A | 11/1994 | Failla et al. |
| 5,374,277 A | 12/1994 | Hassler |
| 5,376,089 A | 12/1994 | Smith |
| 5,376,094 A | 12/1994 | Kline |
| D354,564 S | 1/1995 | Medema |
| 5,383,875 A | 1/1995 | Bays et al. |
| 5,383,880 A | 1/1995 | Hooven |
| 5,383,897 A | 1/1995 | Wholey |
| 5,389,098 A | 2/1995 | Tsuruta et al. |
| 5,389,103 A | 2/1995 | Melzer et al. |
| 5,389,104 A | 2/1995 | Hahnen et al. |
| 5,391,166 A | 2/1995 | Eggers |
| 5,391,183 A | 2/1995 | Janzen et al. |
| 5,395,360 A | 3/1995 | Manoukian |
| 5,396,900 A | 3/1995 | Slater et al. |
| 5,397,325 A | 3/1995 | Della Badia et al. |
| 5,403,312 A | 4/1995 | Yates et al. |
| 5,403,342 A | 4/1995 | Tovey et al. |
| 5,405,344 A | 4/1995 | Williamson et al. |
| 5,409,763 A | 4/1995 | Serizawa et al. |
| D358,887 S | 5/1995 | Feinberg |
| 5,411,519 A | 5/1995 | Tovey et al. |
| 5,411,520 A | 5/1995 | Nash et al. |
| 5,413,571 A | 5/1995 | Katsaros et al. |
| 5,415,656 A | 5/1995 | Tihon et al. |
| 5,415,657 A | 5/1995 | Taymor-Luria |
| 5,417,709 A | 5/1995 | Slater |
| 5,422,567 A | 6/1995 | Matsunaga |
| 5,423,810 A | 6/1995 | Goble et al. |
| 5,425,690 A | 6/1995 | Chang |
| 5,425,739 A | 6/1995 | Jessen |
| 5,429,616 A | 7/1995 | Schaffer |
| 5,431,672 A | 7/1995 | Cote et al. |
| 5,431,674 A | 7/1995 | Basile et al. |
| 5,437,277 A | 8/1995 | Dumoulin et al. |
| 5,437,292 A | 8/1995 | Kipshidze et al. |
| 5,438,302 A | 8/1995 | Goble |
| 5,439,478 A | 8/1995 | Palmer |
| 5,441,059 A | 8/1995 | Dannan |
| 5,441,517 A | 8/1995 | Kensey et al. |
| 5,443,463 A | 8/1995 | Stern et al. |
| 5,443,464 A | 8/1995 | Russell et al. |
| 5,443,479 A | 8/1995 | Bressi, Jr. |
| 5,443,480 A | 8/1995 | Jacobs et al. |
| 5,445,638 A | 8/1995 | Rydell et al. |
| 5,445,658 A | 8/1995 | Durrfeld et al. |
| 5,449,480 A | 9/1995 | Kuriya et al. |
| 5,451,224 A | 9/1995 | Goble et al. |
| 5,454,809 A | 10/1995 | Janssen |
| 5,454,823 A | 10/1995 | Richardson et al. |
| 5,454,827 A | 10/1995 | Aust et al. |
| 5,456,684 A | 10/1995 | Schmidt et al. |
| 5,458,598 A | 10/1995 | Feinberg et al. |
| 5,460,629 A | 10/1995 | Shlain et al. |
| 5,461,765 A | 10/1995 | Linden et al. |
| 5,462,546 A | 10/1995 | Rydell |
| 5,472,442 A | 12/1995 | Klicek |
| 5,472,443 A | 12/1995 | Cordis et al. |
| 5,476,479 A | 12/1995 | Green et al. |
| 5,478,351 A | 12/1995 | Meade et al. |
| 5,480,406 A | 1/1996 | Nolan et al. |
| 5,480,409 A | 1/1996 | Riza |
| 5,482,054 A | 1/1996 | Slater et al. |
| 5,484,436 A | 1/1996 | Eggers et al. |
| 5,493,899 A | 2/1996 | Beck et al. |
| 5,496,312 A | 3/1996 | Klicek |

(56) References Cited

U.S. PATENT DOCUMENTS

| | | |
|---|---|---|
| 5,496,317 A | 3/1996 | Goble et al. |
| 5,496,347 A | 3/1996 | Hashiguchi et al. |
| 5,499,997 A | 3/1996 | Sharpe et al. |
| 5,501,654 A | 3/1996 | Failla et al. |
| 5,509,922 A | 4/1996 | Aranyi et al. |
| 5,512,721 A | 4/1996 | Young et al. |
| 5,514,134 A | 5/1996 | Rydell et al. |
| 5,520,702 A | 5/1996 | Sauer et al. |
| 5,527,313 A | 6/1996 | Scott et al. |
| 5,528,833 A | 6/1996 | Sakuma |
| 5,529,067 A | 6/1996 | Larsen et al. |
| 5,531,744 A | 7/1996 | Nardella et al. |
| 5,536,251 A | 7/1996 | Evard et al. |
| 5,540,684 A | 7/1996 | Hassler, Jr. |
| 5,540,685 A | 7/1996 | Parins et al. |
| 5,540,706 A | 7/1996 | Aust et al. |
| 5,540,715 A | 7/1996 | Katsaros et al. |
| 5,542,945 A | 8/1996 | Fritzsch |
| 5,549,604 A | 8/1996 | Sutcu et al. |
| 5,554,172 A | 9/1996 | Horner et al. |
| 5,558,671 A | 9/1996 | Yates |
| 5,558,672 A | 9/1996 | Edwards et al. |
| 5,562,619 A | 10/1996 | Mirarchi et al. |
| 5,562,699 A | 10/1996 | Heimberger et al. |
| 5,562,720 A | 10/1996 | Stern et al. |
| 5,564,615 A | 10/1996 | Bishop et al. |
| 5,568,859 A | 10/1996 | Levy et al. |
| 5,569,241 A | 10/1996 | Edwards |
| 5,569,243 A | 10/1996 | Kortenbach et al. |
| 5,571,100 A | 11/1996 | Goble et al. |
| 5,573,424 A | 11/1996 | Poppe |
| 5,573,534 A | 11/1996 | Stone |
| 5,573,535 A | 11/1996 | Viklund |
| 5,575,799 A | 11/1996 | Bolanos et al. |
| 5,575,805 A | 11/1996 | Li |
| 5,578,052 A | 11/1996 | Koros et al. |
| 5,579,781 A | 12/1996 | Cooke |
| 5,582,611 A | 12/1996 | Tsuruta et al. |
| 5,582,617 A | 12/1996 | Klieman et al. |
| 5,585,896 A | 12/1996 | Yamazaki et al. |
| 5,590,570 A | 1/1997 | LeMaire, III et al. |
| 5,591,181 A | 1/1997 | Stone et al. |
| 5,597,107 A | 1/1997 | Knodel et al. |
| 5,599,350 A | 2/1997 | Schulze et al. |
| 5,601,224 A | 2/1997 | Bishop et al. |
| 5,601,601 A | 2/1997 | Tal et al. |
| 5,601,641 A | 2/1997 | Stephens |
| 5,603,711 A | 2/1997 | Parins et al. |
| 5,603,723 A | 2/1997 | Aranyi et al. |
| 5,607,436 A | 3/1997 | Pratt et al. |
| 5,611,798 A | 3/1997 | Eggers |
| 5,611,808 A | 3/1997 | Hossain et al. |
| 5,611,813 A | 3/1997 | Lichtman |
| 5,618,294 A | 4/1997 | Aust et al. |
| 5,618,307 A | 4/1997 | Donlon et al. |
| 5,620,415 A | 4/1997 | Lucey et al. |
| 5,620,453 A | 4/1997 | Nallakrishnan |
| 5,620,459 A | 4/1997 | Lichtman |
| 5,624,452 A | 4/1997 | Yates |
| 5,626,578 A | 5/1997 | Tihon |
| 5,626,607 A | 5/1997 | Malecki et al. |
| 5,626,609 A | 5/1997 | Zvenyatsky et al. |
| 5,630,833 A | 5/1997 | Katsaros et al. |
| 5,637,110 A | 6/1997 | Pennybacker et al. |
| 5,637,111 A | 6/1997 | Sutcu et al. |
| 5,638,003 A | 6/1997 | Hall |
| 5,638,827 A | 6/1997 | Palmer et al. |
| 5,639,403 A | 6/1997 | Ida et al. |
| 5,643,294 A | 7/1997 | Tovey et al. |
| 5,647,869 A | 7/1997 | Goble et al. |
| 5,647,871 A | 7/1997 | Levine et al. |
| 5,649,959 A | 7/1997 | Hannam et al. |
| 5,655,650 A | 8/1997 | Naitou |
| 5,658,281 A | 8/1997 | Heard |
| D384,413 S | 9/1997 | Zlock et al. |
| 5,662,667 A | 9/1997 | Knodel |
| 5,665,100 A | 9/1997 | Yoon |
| 5,667,526 A | 9/1997 | Levin |
| 5,673,841 A | 10/1997 | Schulze et al. |
| 5,674,220 A | 10/1997 | Fox et al. |
| 5,674,229 A | 10/1997 | Tovey et al. |
| 5,681,282 A | 10/1997 | Eggers et al. |
| 5,688,270 A | 11/1997 | Yates et al. |
| 5,690,652 A | 11/1997 | Wurster et al. |
| 5,690,653 A | 11/1997 | Richardson et al. |
| 5,693,051 A | 12/1997 | Schulze et al. |
| 5,693,920 A | 12/1997 | Maeda |
| 5,695,522 A | 12/1997 | LeMaire, III et al. |
| 5,700,261 A | 12/1997 | Brinkerhoff |
| 5,700,270 A | 12/1997 | Peyser et al. |
| 5,702,390 A | 12/1997 | Austin et al. |
| 5,707,369 A | 1/1998 | Vaitekunas et al. |
| 5,709,680 A | 1/1998 | Yates et al. |
| 5,713,895 A | 2/1998 | Lontine et al. |
| 5,716,366 A | 2/1998 | Yates |
| 5,720,742 A | 2/1998 | Zacharias |
| 5,720,744 A | 2/1998 | Eggleston et al. |
| 5,722,421 A | 3/1998 | Francese et al. |
| 5,725,536 A | 3/1998 | Oberlin et al. |
| 5,727,428 A | 3/1998 | LeMaire, III et al. |
| H1745 H | 4/1998 | Paraschac |
| 5,735,848 A | 4/1998 | Yates et al. |
| 5,735,849 A | 4/1998 | Baden et al. |
| 5,743,906 A | 4/1998 | Parins et al. |
| 5,752,973 A | 5/1998 | Kieturakis |
| 5,755,717 A | 5/1998 | Yates et al. |
| 5,759,188 A | 6/1998 | Yoon |
| 5,762,255 A | 6/1998 | Chrisman et al. |
| 5,762,609 A | 6/1998 | Benaron et al. |
| 5,766,130 A | 6/1998 | Selmonosky |
| 5,766,166 A | 6/1998 | Hooven |
| 5,766,170 A | 6/1998 | Eggers |
| 5,766,196 A | 6/1998 | Griffiths |
| 5,769,841 A * | 6/1998 | Odell .............. A61B 18/1206 606/1 |
| 5,769,849 A | 6/1998 | Eggers |
| 5,772,655 A | 6/1998 | Bauer et al. |
| 5,772,670 A | 6/1998 | Brosa |
| 5,776,128 A | 7/1998 | Eggers |
| 5,776,130 A | 7/1998 | Buysse et al. |
| 5,776,156 A | 7/1998 | Shikhman |
| 5,779,646 A | 7/1998 | Koblish et al. |
| 5,779,701 A | 7/1998 | McBrayer et al. |
| 5,779,727 A | 7/1998 | Orejola |
| 5,781,048 A | 7/1998 | Nakao et al. |
| 5,791,231 A | 8/1998 | Cohn et al. |
| 5,792,137 A | 8/1998 | Carr et al. |
| 5,792,165 A | 8/1998 | Klieman et al. |
| 5,792,177 A | 8/1998 | Kaseda |
| 5,797,537 A | 8/1998 | Oberlin et al. |
| 5,797,927 A | 8/1998 | Yoon |
| 5,797,938 A | 8/1998 | Paraschac et al. |
| 5,797,941 A | 8/1998 | Schulze et al. |
| 5,797,958 A | 8/1998 | Yoon |
| 5,797,959 A | 8/1998 | Castro et al. |
| 5,800,448 A | 9/1998 | Banko |
| 5,800,449 A | 9/1998 | Wales |
| 5,807,393 A | 9/1998 | Williamson, IV et al. |
| 5,810,764 A | 9/1998 | Eggers et al. |
| 5,810,805 A | 9/1998 | Sutcu et al. |
| 5,810,808 A | 9/1998 | Eggers |
| 5,810,811 A | 9/1998 | Yates et al. |
| 5,810,877 A | 9/1998 | Roth et al. |
| 5,814,043 A | 9/1998 | Shapeton |
| 5,814,054 A | 9/1998 | Kortenbach et al. |
| 5,817,083 A | 10/1998 | Shemesh et al. |
| 5,817,119 A | 10/1998 | Klieman et al. |
| 5,820,630 A | 10/1998 | Lind |
| 5,824,978 A | 10/1998 | Karasik et al. |
| 5,827,271 A | 10/1998 | Buysse et al. |
| 5,827,274 A | 10/1998 | Bonnet et al. |
| 5,827,279 A | 10/1998 | Hughett et al. |
| 5,827,281 A | 10/1998 | Levin |
| 5,827,323 A | 10/1998 | Klieman et al. |

(56) References Cited

U.S. PATENT DOCUMENTS

| | | |
|---|---|---|
| 5,827,548 A | 10/1998 | Lavallee et al. |
| 5,830,212 A | 11/1998 | Cartmell et al. |
| 5,833,690 A | 11/1998 | Yates et al. |
| 5,833,695 A | 11/1998 | Yoon |
| 5,836,072 A | 11/1998 | Sullivan et al. |
| D402,028 S | 12/1998 | Grimm et al. |
| 5,843,080 A | 12/1998 | Fleenor et al. |
| 5,849,020 A | 12/1998 | Long et al. |
| 5,849,022 A | 12/1998 | Sakashita et al. |
| 5,851,214 A | 12/1998 | Larsen et al. |
| 5,853,412 A | 12/1998 | Mayenberger |
| 5,859,527 A | 1/1999 | Cook |
| 5,860,976 A | 1/1999 | Billings et al. |
| 5,865,361 A | 2/1999 | Milliman et al. |
| 5,876,401 A | 3/1999 | Schulze et al. |
| 5,876,410 A | 3/1999 | Petillo |
| 5,876,412 A | 3/1999 | Piraka |
| 5,882,567 A | 3/1999 | Cavallaro et al. |
| D408,018 S | 4/1999 | McNaughton |
| 5,891,141 A | 4/1999 | Rydell |
| 5,891,142 A | 4/1999 | Eggers et al. |
| 5,893,848 A | 4/1999 | Negus et al. |
| 5,893,863 A | 4/1999 | Yoon |
| 5,893,875 A * | 4/1999 | O'Connor ............... A61B 17/29 606/167 |
| 5,893,877 A | 4/1999 | Gampp, Jr. et al. |
| 5,897,563 A | 4/1999 | Yoon et al. |
| 5,902,301 A | 5/1999 | Olig |
| 5,906,630 A | 5/1999 | Anderhub et al. |
| 5,907,140 A | 5/1999 | Smith |
| 5,908,420 A | 6/1999 | Parins et al. |
| 5,908,432 A | 6/1999 | Pan |
| 5,911,719 A | 6/1999 | Eggers |
| 5,913,874 A | 6/1999 | Berns et al. |
| 5,921,916 A | 7/1999 | Aeikens et al. |
| 5,921,984 A | 7/1999 | Sutcu et al. |
| 5,925,043 A | 7/1999 | Kumar et al. |
| 5,928,136 A | 7/1999 | Barry |
| 5,935,126 A | 8/1999 | Riza |
| 5,938,589 A | 8/1999 | Wako et al. |
| 5,941,869 A | 8/1999 | Patterson et al. |
| 5,944,718 A | 8/1999 | Austin et al. |
| 5,951,545 A | 9/1999 | Schilling et al. |
| 5,951,546 A | 9/1999 | Lorentzen |
| 5,951,549 A | 9/1999 | Richardson et al. |
| 5,954,720 A | 9/1999 | Wilson et al. |
| 5,954,731 A | 9/1999 | Yoon |
| 5,954,733 A | 9/1999 | Yoon |
| 5,957,923 A | 9/1999 | Hahnen et al. |
| 5,957,937 A | 9/1999 | Yoon |
| 5,960,544 A | 10/1999 | Beyers |
| 5,961,514 A | 10/1999 | Long et al. |
| 5,964,758 A | 10/1999 | Dresden |
| 5,967,997 A | 10/1999 | Turturro et al. |
| D416,089 S | 11/1999 | Barton et al. |
| 5,976,132 A | 11/1999 | Morris |
| 5,984,932 A | 11/1999 | Yoon |
| 5,984,938 A | 11/1999 | Yoon |
| 5,984,939 A | 11/1999 | Yoon |
| 5,989,277 A | 11/1999 | LeMaire, III et al. |
| 5,993,466 A | 11/1999 | Yoon |
| 5,993,467 A | 11/1999 | Yoon |
| 5,993,474 A | 11/1999 | Ouchi |
| 5,997,565 A | 12/1999 | Inoue |
| 6,003,517 A | 12/1999 | Sheffield et al. |
| 6,004,332 A | 12/1999 | Yoon et al. |
| 6,004,335 A | 12/1999 | Vaitekunas et al. |
| 6,010,516 A | 1/2000 | Hulka |
| 6,010,519 A | 1/2000 | Mawhirt et al. |
| 6,017,354 A | 1/2000 | Culp et al. |
| 6,017,358 A | 1/2000 | Yoon et al. |
| 6,021,693 A | 2/2000 | Feng-Sing |
| 6,024,741 A | 2/2000 | Williamson, IV et al. |
| 6,024,743 A | 2/2000 | Edwards |
| 6,024,744 A | 2/2000 | Kese et al. |
| 6,027,522 A | 2/2000 | Palmer |
| 6,030,384 A | 2/2000 | Nezhat |
| 6,033,399 A | 3/2000 | Gines |
| 6,039,733 A | 3/2000 | Buysse et al. |
| 6,041,679 A | 3/2000 | Slater et al. |
| 6,050,995 A | 4/2000 | Durgin |
| 6,050,996 A | 4/2000 | Schmaltz et al. |
| 6,053,914 A | 4/2000 | Eggers et al. |
| 6,053,933 A | 4/2000 | Balazs et al. |
| D424,694 S | 5/2000 | Tetzlaff et al. |
| D425,201 S | 5/2000 | Tetzlaff et al. |
| 6,059,782 A | 5/2000 | Novak et al. |
| 6,063,103 A | 5/2000 | Hashiguchi |
| 6,066,139 A | 5/2000 | Ryan et al. |
| 6,071,283 A | 6/2000 | Nardella et al. |
| 6,074,386 A | 6/2000 | Goble et al. |
| 6,077,287 A | 6/2000 | Taylor et al. |
| 6,080,180 A | 6/2000 | Yoon et al. |
| RE36,795 E | 7/2000 | Rydell |
| 6,083,150 A | 7/2000 | Aznoian et al. |
| 6,083,223 A | 7/2000 | Baker |
| 6,086,586 A | 7/2000 | Hooven |
| 6,086,601 A | 7/2000 | Yoon |
| 6,090,107 A | 7/2000 | Borgmeier et al. |
| 6,090,123 A | 7/2000 | Culp et al. |
| 6,096,037 A | 8/2000 | Mulier et al. |
| 6,099,537 A | 8/2000 | Sugai et al. |
| 6,099,550 A | 8/2000 | Yoon |
| 6,102,909 A | 8/2000 | Chen et al. |
| 6,106,542 A | 8/2000 | Toybin et al. |
| 6,110,171 A | 8/2000 | Rydell |
| 6,113,596 A | 9/2000 | Hooven et al. |
| 6,113,598 A | 9/2000 | Baker |
| 6,117,158 A | 9/2000 | Measamer et al. |
| 6,122,549 A | 9/2000 | Sharkey et al. |
| 6,123,701 A | 9/2000 | Nezhat |
| H1904 H | 10/2000 | Yates et al. |
| 6,126,658 A | 10/2000 | Baker |
| 6,126,665 A | 10/2000 | Yoon |
| 6,139,563 A | 10/2000 | Cosgrove, III et al. |
| 6,143,005 A | 11/2000 | Yoon et al. |
| 6,152,923 A | 11/2000 | Ryan |
| 6,152,924 A | 11/2000 | Parins |
| 6,159,217 A | 12/2000 | Roble et al. |
| 6,162,220 A | 12/2000 | Nezhat |
| 6,171,316 B1 | 1/2001 | Kovac et al. |
| 6,174,309 B1 | 1/2001 | Wrublewski et al. |
| 6,174,310 B1 | 1/2001 | Kirwan, Jr. |
| 6,178,628 B1 | 1/2001 | Clemens et al. |
| 6,179,834 B1 | 1/2001 | Buysse et al. |
| 6,179,837 B1 | 1/2001 | Hooven |
| 6,183,467 B1 | 2/2001 | Shapeton et al. |
| 6,187,003 B1 | 2/2001 | Buysse et al. |
| 6,190,386 B1 | 2/2001 | Rydell |
| 6,190,399 B1 | 2/2001 | Palmer et al. |
| 6,190,400 B1 | 2/2001 | Van De Moer et al. |
| 6,193,709 B1 | 2/2001 | Miyawaki et al. |
| 6,193,718 B1 | 2/2001 | Kortenbach et al. |
| 6,206,876 B1 | 3/2001 | Levine et al. |
| 6,206,877 B1 | 3/2001 | Kese et al. |
| 6,206,893 B1 | 3/2001 | Klein et al. |
| 6,214,028 B1 | 4/2001 | Yoon et al. |
| 6,217,602 B1 | 4/2001 | Redmon |
| 6,217,615 B1 | 4/2001 | Sioshansi et al. |
| 6,221,039 B1 | 4/2001 | Durgin et al. |
| 6,223,100 B1 | 4/2001 | Green |
| 6,224,593 B1 | 5/2001 | Ryan et al. |
| 6,224,614 B1 | 5/2001 | Yoon |
| 6,228,080 B1 | 5/2001 | Gines |
| 6,228,083 B1 | 5/2001 | Lands et al. |
| 6,248,124 B1 | 6/2001 | Pedros et al. |
| 6,248,944 B1 | 6/2001 | Ito |
| 6,261,307 B1 | 7/2001 | Yoon et al. |
| 6,267,758 B1 | 7/2001 | Daw et al. |
| 6,267,761 B1 | 7/2001 | Ryan |
| 6,270,497 B1 | 8/2001 | Sekino et al. |
| 6,270,508 B1 | 8/2001 | Klieman et al. |
| 6,273,887 B1 | 8/2001 | Yamauchi et al. |
| 6,277,117 B1 | 8/2001 | Tetzlaff et al. |

(56) References Cited

U.S. PATENT DOCUMENTS

| | | |
|---|---|---|
| 6,280,458 B1 | 8/2001 | Bache et al. |
| 6,283,961 B1 | 9/2001 | Underwood et al. |
| D449,886 S | 10/2001 | Tetzlaff et al. |
| 6,298,550 B1 | 10/2001 | Kirwan, Jr. |
| 6,302,424 B1 | 10/2001 | Gisinger et al. |
| 6,309,404 B1 | 10/2001 | Krzyzanowski |
| 6,319,262 B1 | 11/2001 | Bates et al. |
| 6,319,451 B1 | 11/2001 | Brune |
| 6,322,561 B1 | 11/2001 | Eggers et al. |
| 6,322,580 B1 | 11/2001 | Kanner |
| 6,325,795 B1 | 12/2001 | Lindemann et al. |
| 6,329,778 B1 | 12/2001 | Culp et al. |
| 6,334,860 B1 | 1/2002 | Dorn |
| 6,334,861 B1 | 1/2002 | Chandler et al. |
| D453,923 S | 2/2002 | Olson |
| 6,345,532 B1 | 2/2002 | Coudray et al. |
| 6,350,264 B1 | 2/2002 | Hooven |
| D454,951 S | 3/2002 | Bon |
| 6,352,536 B1 | 3/2002 | Buysse et al. |
| 6,358,249 B1 | 3/2002 | Chen et al. |
| 6,358,259 B1 | 3/2002 | Swain et al. |
| 6,358,268 B1 | 3/2002 | Hunt et al. |
| 6,361,534 B1 | 3/2002 | Chen et al. |
| 6,364,876 B1 | 4/2002 | Erb et al. |
| 6,364,879 B1 | 4/2002 | Chen et al. |
| D457,958 S | 5/2002 | Dycus et al. |
| D457,959 S | 5/2002 | Tetzlaff et al. |
| 6,385,265 B1 | 5/2002 | Duffy et al. |
| 6,387,094 B1 | 5/2002 | Eitenmuller |
| 6,391,035 B1 | 5/2002 | Appleby et al. |
| 6,398,779 B1 | 6/2002 | Buysse et al. |
| 6,402,747 B1 | 6/2002 | Lindemann et al. |
| 6,409,728 B1 | 6/2002 | Ehr et al. |
| H2037 H | 7/2002 | Yates et al. |
| 6,419,675 B1 | 7/2002 | Gallo, Sr. |
| 6,425,896 B1 | 7/2002 | Baltschun et al. |
| 6,432,112 B2 | 8/2002 | Brock et al. |
| 6,440,130 B1 | 8/2002 | Mulier et al. |
| 6,440,144 B1 | 8/2002 | Bacher |
| 6,443,952 B1 | 9/2002 | Mulier et al. |
| 6,443,970 B1 | 9/2002 | Schulze et al. |
| 6,451,018 B1 | 9/2002 | Lands et al. |
| 6,458,125 B1 | 10/2002 | Cosmescu |
| 6,458,128 B1 | 10/2002 | Schulze |
| 6,458,129 B2 | 10/2002 | Scarfi |
| 6,458,130 B1 | 10/2002 | Frazier et al. |
| 6,461,352 B2 | 10/2002 | Morgan et al. |
| 6,461,368 B2 | 10/2002 | Fogarty et al. |
| 6,464,701 B1 | 10/2002 | Hooven et al. |
| 6,464,702 B2 | 10/2002 | Schulze et al. |
| 6,464,704 B2 | 10/2002 | Schmaltz et al. |
| 6,471,696 B1 | 10/2002 | Berube et al. |
| D465,281 S | 11/2002 | Lang |
| D466,209 S | 11/2002 | Bon |
| 6,485,489 B2 | 11/2002 | Teirstein et al. |
| 6,488,680 B1 | 12/2002 | Francischelli et al. |
| 6,494,877 B2 | 12/2002 | Odell et al. |
| 6,494,888 B1 | 12/2002 | Laufer et al. |
| 6,500,176 B1 | 12/2002 | Truckai et al. |
| 6,506,196 B1 | 1/2003 | Laufer |
| 6,508,815 B1 | 1/2003 | Strul et al. |
| 6,511,480 B1 | 1/2003 | Tetzlaff et al. |
| 6,514,215 B1 | 2/2003 | Ouchi |
| 6,514,252 B2 | 2/2003 | Nezhat et al. |
| 6,517,536 B2 | 2/2003 | Hooven et al. |
| 6,517,539 B1 | 2/2003 | Smith et al. |
| 6,527,771 B1 | 3/2003 | Weadock et al. |
| 6,533,784 B2 | 3/2003 | Truckai et al. |
| 6,537,272 B2 | 3/2003 | Christopherson et al. |
| 6,540,745 B1 | 4/2003 | Fairbourn et al. |
| 6,545,239 B2 | 4/2003 | Spedale et al. |
| 6,554,844 B2 | 4/2003 | Lee et al. |
| 6,558,385 B1 | 5/2003 | McClurken et al. |
| 6,562,037 B2 | 5/2003 | Paton et al. |
| 6,569,105 B1 | 5/2003 | Kortenbach et al. |
| 6,582,450 B2 | 6/2003 | Ouchi |
| 6,585,735 B1 | 7/2003 | Frazier et al. |
| 6,602,252 B2 | 8/2003 | Mollenauer |
| 6,605,790 B2 | 8/2003 | Yoshida |
| 6,610,060 B2 | 8/2003 | Mulier et al. |
| 6,613,048 B2 | 9/2003 | Mulier et al. |
| 6,616,654 B2 | 9/2003 | Mollenauer |
| 6,616,658 B2 | 9/2003 | Ineson |
| 6,616,661 B2 | 9/2003 | Wellman et al. |
| 6,620,161 B2 | 9/2003 | Schulze et al. |
| 6,620,184 B2 | 9/2003 | de Laforcade et al. |
| 6,623,482 B2 | 9/2003 | Pendekanti et al. |
| 6,626,901 B1 | 9/2003 | Treat et al. |
| 6,629,534 B1 | 10/2003 | St. Goar et al. |
| 6,638,287 B2 | 10/2003 | Danitz et al. |
| 6,641,595 B1 | 11/2003 | Moran et al. |
| 6,652,514 B2 | 11/2003 | Ellman et al. |
| 6,652,518 B2 | 11/2003 | Wellman et al. |
| 6,652,521 B2 | 11/2003 | Schulze |
| 6,656,173 B1 | 12/2003 | Palermo |
| 6,656,175 B2 | 12/2003 | Francischelli et al. |
| 6,656,177 B2 | 12/2003 | Truckai et al. |
| 6,660,072 B2 | 12/2003 | Chatterjee |
| 6,663,639 B1 | 12/2003 | Laufer et al. |
| 6,663,641 B1 | 12/2003 | Kovac et al. |
| 6,666,854 B1 | 12/2003 | Lange |
| 6,669,696 B2 | 12/2003 | Bacher et al. |
| 6,673,092 B1 | 1/2004 | Bacher |
| 6,676,660 B2 | 1/2004 | Wampler et al. |
| 6,676,676 B2 | 1/2004 | Danitz et al. |
| 6,679,882 B1 | 1/2004 | Kornerup |
| 6,682,527 B2 | 1/2004 | Strul |
| 6,682,528 B2 | 1/2004 | Frazier et al. |
| 6,685,704 B2 | 2/2004 | Greep |
| 6,685,724 B1 | 2/2004 | Haluck |
| 6,689,131 B2 | 2/2004 | McClurken |
| 6,692,445 B2 | 2/2004 | Roberts et al. |
| 6,693,246 B1 | 2/2004 | Rudolph et al. |
| 6,695,840 B2 | 2/2004 | Schulze |
| 6,702,810 B2 | 3/2004 | McClurken et al. |
| 6,723,092 B2 | 4/2004 | Brown et al. |
| 6,726,068 B2 | 4/2004 | Miller |
| 6,726,686 B2 | 4/2004 | Buysse et al. |
| 6,726,694 B2 | 4/2004 | Blatter et al. |
| 6,733,498 B2 | 5/2004 | Paton et al. |
| 6,733,501 B2 | 5/2004 | Levine |
| 6,736,813 B2 | 5/2004 | Yamauchi et al. |
| 6,743,229 B2 | 6/2004 | Buysse et al. |
| 6,743,230 B2 | 6/2004 | Lutze et al. |
| 6,743,239 B1 | 6/2004 | Kuehn et al. |
| 6,743,240 B2 | 6/2004 | Smith et al. |
| 6,755,338 B2 | 6/2004 | Hahnen et al. |
| 6,755,824 B2 | 6/2004 | Jain et al. |
| 6,755,843 B2 | 6/2004 | Chung et al. |
| 6,756,553 B1 | 6/2004 | Yamaguchi et al. |
| 6,757,977 B2 | 7/2004 | Dambal et al. |
| D493,888 S | 8/2004 | Reschke |
| 6,770,072 B2 | 8/2004 | Truckai et al. |
| 6,773,409 B2 | 8/2004 | Truckai et al. |
| 6,773,432 B1 | 8/2004 | Clayman et al. |
| 6,773,434 B2 | 8/2004 | Ciarrocca |
| 6,773,435 B2 | 8/2004 | Schulze et al. |
| 6,773,441 B1 | 8/2004 | Laufer et al. |
| 6,775,575 B2 | 8/2004 | Bommannan et al. |
| 6,776,780 B2 | 8/2004 | Mulier et al. |
| 6,784,405 B2 | 8/2004 | Flugstad et al. |
| 6,786,905 B2 | 9/2004 | Swanson et al. |
| 6,790,217 B2 | 9/2004 | Schulze et al. |
| 6,796,981 B2 | 9/2004 | Wham et al. |
| D496,997 S | 10/2004 | Dycus et al. |
| 6,800,825 B1 | 10/2004 | Sasaki et al. |
| 6,802,843 B2 | 10/2004 | Truckai et al. |
| 6,808,525 B2 | 10/2004 | Latterell et al. |
| D499,181 S | 11/2004 | Dycus et al. |
| 6,818,000 B2 | 11/2004 | Muller et al. |
| 6,818,007 B1 | 11/2004 | Dampney et al. |
| 6,821,273 B2 | 11/2004 | Mollenauer |
| 6,821,285 B2 | 11/2004 | Laufer et al. |
| 6,824,547 B2 | 11/2004 | Wilson, Jr. et al. |

(56) References Cited

U.S. PATENT DOCUMENTS

| | | | |
|---|---|---|---|
| 6,830,174 B2 | 12/2004 | Hillstead et al. |
| 6,835,200 B2 | 12/2004 | Laufer et al. |
| 6,843,789 B2 | 1/2005 | Goble |
| 6,857,357 B2 | 2/2005 | Fujii |
| 6,858,028 B2 | 2/2005 | Mulier et al. |
| D502,994 S | 3/2005 | Blake, III |
| 6,860,880 B2 | 3/2005 | Treat et al. |
| 6,878,147 B2 | 4/2005 | Prakash et al. |
| 6,887,240 B1 | 5/2005 | Lands et al. |
| 6,889,116 B2 | 5/2005 | Jinno |
| 6,905,497 B2 | 6/2005 | Truckai et al. |
| 6,908,463 B2 | 6/2005 | Treat et al. |
| 6,914,201 B2 | 7/2005 | Van Vooren et al. |
| 6,916,314 B2 * | 7/2005 | Schneider ........ A61B 17/00234 606/1 |
| 6,926,716 B2 | 8/2005 | Baker et al. |
| 6,929,644 B2 | 8/2005 | Truckai et al. |
| 6,932,810 B2 | 8/2005 | Ryan |
| 6,932,816 B2 | 8/2005 | Phan |
| 6,934,134 B2 | 8/2005 | Mod et al. |
| 6,936,061 B2 | 8/2005 | Sasaki |
| D509,297 S | 9/2005 | Wells |
| 6,942,662 B2 | 9/2005 | Goble et al. |
| 6,943,311 B2 | 9/2005 | Miyako |
| 6,951,559 B1 | 10/2005 | Greep |
| 6,953,430 B2 | 10/2005 | Kidooka |
| 6,953,461 B2 | 10/2005 | McClurken et al. |
| 6,958,070 B2 | 10/2005 | Witt et al. |
| 6,960,210 B2 | 11/2005 | Lands et al. |
| 6,964,662 B2 | 11/2005 | Kidooka |
| 6,966,907 B2 | 11/2005 | Goble |
| 6,972,017 B2 | 12/2005 | Smith et al. |
| 6,974,452 B1 | 12/2005 | Gille et al. |
| 6,976,492 B2 | 12/2005 | Ingle et al. |
| 6,977,495 B2 | 12/2005 | Donofrio |
| 6,979,786 B2 | 12/2005 | Aukland et al. |
| 6,981,628 B2 | 1/2006 | Wales |
| 6,987,244 B2 | 1/2006 | Bauer |
| 6,989,017 B2 | 1/2006 | Howell et al. |
| 6,994,707 B2 | 2/2006 | Ellman et al. |
| 6,994,709 B2 | 2/2006 | Iida |
| 6,997,931 B2 | 2/2006 | Sauer et al. |
| 7,001,381 B2 | 2/2006 | Harano et al. |
| 7,001,408 B2 | 2/2006 | Knodel et al. |
| 7,011,657 B2 | 3/2006 | Truckai et al. |
| 7,025,763 B2 | 4/2006 | Karasawa et al. |
| 7,033,354 B2 | 4/2006 | Keppel |
| 7,033,356 B2 | 4/2006 | Latterell et al. |
| 7,041,102 B2 | 5/2006 | Truckai et al. |
| 7,044,948 B2 | 5/2006 | Keppel |
| 7,052,489 B2 | 5/2006 | Griego et al. |
| 7,052,496 B2 | 5/2006 | Yamauchi |
| 7,063,699 B2 | 6/2006 | Hess et al. |
| 7,063,715 B2 | 6/2006 | Onuki et al. |
| D525,361 S | 7/2006 | Hushka |
| 7,070,597 B2 | 7/2006 | Truckai et al. |
| 7,083,618 B2 | 8/2006 | Couture et al. |
| 7,083,619 B2 | 8/2006 | Truckai et al. |
| 7,083,620 B2 | 8/2006 | Jahns et al. |
| 7,087,051 B2 | 8/2006 | Bourne et al. |
| 7,087,054 B2 | 8/2006 | Truckai et al. |
| 7,090,673 B2 | 8/2006 | Dycus et al. |
| 7,090,689 B2 | 8/2006 | Nagase et al. |
| 7,101,371 B2 | 9/2006 | Dycus et al. |
| 7,101,372 B2 | 9/2006 | Dycus et al. |
| 7,101,373 B2 | 9/2006 | Dycus et al. |
| 7,103,947 B2 | 9/2006 | Sartor et al. |
| 7,107,124 B2 | 9/2006 | Green |
| 7,108,694 B2 | 9/2006 | Miura et al. |
| 7,112,199 B2 | 9/2006 | Cosmescu |
| 7,112,201 B2 | 9/2006 | Truckai et al. |
| D531,311 S | 10/2006 | Guerra et al. |
| 7,115,123 B2 | 10/2006 | Knowlton et al. |
| 7,115,139 B2 | 10/2006 | McClurken et al. |
| 7,118,570 B2 | 10/2006 | Tetzlaff et al. |
| 7,118,587 B2 | 10/2006 | Dycus et al. |
| 7,131,860 B2 | 11/2006 | Sartor et al. |
| 7,131,970 B2 | 11/2006 | Moses et al. |
| 7,131,971 B2 | 11/2006 | Dycus et al. |
| 7,135,018 B2 | 11/2006 | Ryan et al. |
| 7,135,020 B2 | 11/2006 | Lawes et al. |
| 7,137,980 B2 | 11/2006 | Buysse et al. |
| D533,274 S | 12/2006 | Visconti et al. |
| D533,942 S | 12/2006 | Kerr et al. |
| 7,145,757 B2 | 12/2006 | Shea et al. |
| 7,147,632 B2 | 12/2006 | Prakash et al. |
| 7,147,638 B2 | 12/2006 | Chapman et al. |
| 7,150,097 B2 | 12/2006 | Sremcich et al. |
| 7,150,749 B2 | 12/2006 | Dycus et al. |
| 7,153,314 B2 | 12/2006 | Laufer et al. |
| D535,027 S | 1/2007 | James et al. |
| 7,156,842 B2 | 1/2007 | Sartor et al. |
| 7,156,846 B2 | 1/2007 | Dycus et al. |
| 7,160,298 B2 | 1/2007 | Lawes et al. |
| 7,160,299 B2 | 1/2007 | Baily |
| 7,166,106 B2 | 1/2007 | Bartel et al. |
| 7,169,145 B2 | 1/2007 | Isaacson et al. |
| 7,169,146 B2 | 1/2007 | Truckai et al. |
| 7,179,255 B2 | 2/2007 | Lettice et al. |
| 7,179,258 B2 | 2/2007 | Buysse et al. |
| 7,184,820 B2 | 2/2007 | Jersey-Willuhn et al. |
| D538,932 S | 3/2007 | Malik |
| 7,189,233 B2 | 3/2007 | Truckai et al. |
| 7,195,631 B2 | 3/2007 | Dumbauld |
| D541,418 S | 4/2007 | Schechter et al. |
| 7,204,835 B2 | 4/2007 | Latterell et al. |
| 7,207,990 B2 | 4/2007 | Lands et al. |
| 7,208,005 B2 | 4/2007 | Frecker et al. |
| D541,611 S | 5/2007 | Aglassinger |
| D541,938 S | 5/2007 | Kerr et al. |
| 7,211,084 B2 | 5/2007 | Goble et al. |
| 7,223,264 B2 | 5/2007 | Daniel et al. |
| 7,223,265 B2 | 5/2007 | Keppel |
| D545,432 S | 6/2007 | Watanabe |
| 7,232,440 B2 | 6/2007 | Dumbauld et al. |
| D547,154 S | 7/2007 | Lee |
| 7,238,184 B2 | 7/2007 | Megerman et al. |
| 7,241,288 B2 | 7/2007 | Braun |
| 7,241,296 B2 | 7/2007 | Buysse et al. |
| 7,244,257 B2 | 7/2007 | Podhajsky et al. |
| 7,246,734 B2 | 7/2007 | Shelton, IV |
| 7,248,944 B2 | 7/2007 | Green |
| 7,252,667 B2 | 8/2007 | Moses et al. |
| 7,254,433 B2 | 8/2007 | Diab et al. |
| 7,255,697 B2 | 8/2007 | Dycus et al. |
| 7,267,677 B2 | 9/2007 | Johnson et al. |
| 7,270,660 B2 | 9/2007 | Ryan |
| 7,270,664 B2 | 9/2007 | Johnson et al. |
| 7,276,068 B2 | 10/2007 | Johnson et al. |
| 7,288,103 B2 | 10/2007 | Suzuki |
| 7,291,161 B2 | 11/2007 | Hooven |
| 7,300,435 B2 | 11/2007 | Wham et al. |
| 7,303,557 B2 | 12/2007 | Wham et al. |
| 7,311,709 B2 | 12/2007 | Truckai et al. |
| 7,314,471 B2 | 1/2008 | Holman |
| 7,318,823 B2 | 1/2008 | Sharps et al. |
| 7,326,202 B2 | 2/2008 | McGaffigan |
| 7,329,256 B2 | 2/2008 | Johnson et al. |
| 7,329,257 B2 | 2/2008 | Kanehira et al. |
| D564,662 S | 3/2008 | Moses et al. |
| 7,338,526 B2 | 3/2008 | Steinberg |
| 7,342,754 B2 | 3/2008 | Fitzgerald et al. |
| 7,344,268 B2 | 3/2008 | Jigamian |
| 7,347,864 B2 | 3/2008 | Vargas |
| D567,943 S | 4/2008 | Moses et al. |
| 7,354,440 B2 | 4/2008 | Truckai et al. |
| 7,367,976 B2 | 5/2008 | Lawes et al. |
| 7,377,920 B2 | 5/2008 | Buysse et al. |
| 7,384,420 B2 | 6/2008 | Dycus et al. |
| 7,384,421 B2 | 6/2008 | Hushka |
| 7,396,265 B2 | 7/2008 | Darley et al. |
| 7,396,336 B2 | 7/2008 | Orszulak et al. |
| 7,396,356 B2 | 7/2008 | Mollenauer |
| D575,395 S | 8/2008 | Hushka |

(56) References Cited

U.S. PATENT DOCUMENTS

| | | | |
|---|---|---|---|
| D575,401 S | 8/2008 | Hixson et al. |
| 7,422,592 B2 | 9/2008 | Morley et al. |
| 7,425,835 B2 | 9/2008 | Eisele |
| 7,431,721 B2 | 10/2008 | Paton et al. |
| 7,435,249 B2 | 10/2008 | Buysse et al. |
| 7,438,714 B2 | 10/2008 | Phan |
| 7,442,193 B2 | 10/2008 | Shields et al. |
| 7,442,194 B2 | 10/2008 | Dumbauld et al. |
| 7,445,621 B2 | 11/2008 | Dumbauld et al. |
| D582,038 S | 12/2008 | Swoyer et al. |
| 7,458,972 B2 | 12/2008 | Keppel |
| 7,473,253 B2 | 1/2009 | Dycus et al. |
| 7,481,810 B2 | 1/2009 | Dumbauld et al. |
| 7,487,780 B2 | 2/2009 | Hooven |
| 7,491,201 B2 | 2/2009 | Shields et al. |
| 7,491,202 B2 | 2/2009 | Odom et al. |
| 7,500,975 B2 | 3/2009 | Cunningham et al. |
| 7,503,474 B2 | 3/2009 | Hillstead et al. |
| 7,510,556 B2 | 3/2009 | Nguyen et al. |
| 7,513,898 B2 | 4/2009 | Johnson et al. |
| 7,517,351 B2 | 4/2009 | Culp et al. |
| 7,540,872 B2 | 6/2009 | Schechter et al. |
| 7,549,995 B2 | 6/2009 | Schultz |
| 7,553,312 B2 | 6/2009 | Tetzlaff et al. |
| 7,553,686 B2 | 6/2009 | George et al. |
| 7,566,331 B2* | 7/2009 | Looper | A61B 17/320016 606/1 |
| 7,569,626 B2 | 8/2009 | Truckai |
| 7,582,087 B2 | 9/2009 | Tetzlaff et al. |
| 7,588,565 B2 | 9/2009 | Marchitto et al. |
| 7,594,313 B2 | 9/2009 | Prakash et al. |
| 7,594,916 B2 | 9/2009 | Weinberg |
| 7,597,693 B2 | 10/2009 | Garrison |
| 7,621,910 B2 | 11/2009 | Sugi |
| 7,624,186 B2 | 11/2009 | Tanida |
| 7,625,370 B2 | 12/2009 | Hart et al. |
| 7,628,791 B2 | 12/2009 | Garrison et al. |
| 7,628,792 B2 | 12/2009 | Guerra |
| 7,637,409 B2 | 12/2009 | Marczyk |
| 7,641,653 B2 | 1/2010 | Dalla Betta et al. |
| 7,651,493 B2 | 1/2010 | Arts et al. |
| 7,651,494 B2 | 1/2010 | McClurken et al. |
| 7,655,004 B2 | 2/2010 | Long |
| 7,655,007 B2 | 2/2010 | Baily |
| 7,668,597 B2 | 2/2010 | Engmark et al. |
| 7,678,111 B2 | 3/2010 | Mulier et al. |
| 7,686,804 B2 | 3/2010 | Johnson et al. |
| 7,686,827 B2 | 3/2010 | Hushka |
| 7,708,735 B2 | 5/2010 | Chapman et al. |
| 7,717,115 B2 | 5/2010 | Barrett et al. |
| 7,717,904 B2 | 5/2010 | Suzuki et al. |
| 7,717,914 B2 | 5/2010 | Kimura |
| 7,717,915 B2 | 5/2010 | Miyazawa |
| 7,722,607 B2 | 5/2010 | Dumbauld et al. |
| D617,900 S | 6/2010 | Kingsley et al. |
| D617,901 S | 6/2010 | Unger et al. |
| D617,902 S | 6/2010 | Twomey et al. |
| D617,903 S | 6/2010 | Unger et al. |
| D618,798 S | 6/2010 | Olson et al. |
| 7,727,231 B2 | 6/2010 | Swanson |
| 7,731,717 B2 | 6/2010 | Odom et al. |
| 7,736,374 B2 | 6/2010 | Vaughan et al. |
| 7,744,615 B2 | 6/2010 | Couture |
| 7,749,217 B2 | 7/2010 | Podhajsky |
| 7,753,908 B2 | 7/2010 | Swanson |
| 7,753,909 B2 | 7/2010 | Chapman et al. |
| D621,503 S | 8/2010 | Otten et al. |
| 7,766,910 B2 | 8/2010 | Hixson et al. |
| 7,771,425 B2 | 8/2010 | Dycus et al. |
| 7,776,036 B2 | 8/2010 | Schechter et al. |
| 7,776,037 B2 | 8/2010 | Odom |
| 7,780,662 B2 | 8/2010 | Bahney |
| 7,780,663 B2 | 8/2010 | Yates et al. |
| 7,789,878 B2 | 9/2010 | Dumbauld et al. |
| 7,799,026 B2 | 9/2010 | Schechter et al. |
| 7,799,028 B2 | 9/2010 | Schechter et al. |
| 7,811,283 B2 | 10/2010 | Moses et al. |
| 7,819,872 B2 | 10/2010 | Johnson et al. |
| D627,462 S | 11/2010 | Kingsley |
| D628,289 S | 11/2010 | Romero |
| D628,290 S | 11/2010 | Romero |
| 7,828,798 B2 | 11/2010 | Buysse et al. |
| 7,832,408 B2 | 11/2010 | Shelton, IV et al. |
| 7,837,685 B2 | 11/2010 | Weinberg et al. |
| 7,839,674 B2 | 11/2010 | Lowrey et al. |
| 7,842,033 B2 | 11/2010 | Isaacson et al. |
| 7,846,158 B2 | 12/2010 | Podhajsky |
| 7,846,161 B2 | 12/2010 | Dumbauld et al. |
| 7,857,812 B2 | 12/2010 | Dycus et al. |
| D630,324 S | 1/2011 | Reschke |
| 7,877,852 B2 | 2/2011 | Unger et al. |
| 7,877,853 B2 | 2/2011 | Unger et al. |
| 7,879,035 B2 | 2/2011 | Garrison et al. |
| 7,887,535 B2 | 2/2011 | Lands et al. |
| 7,887,536 B2 | 2/2011 | Johnson et al. |
| 7,896,878 B2 | 3/2011 | Johnson et al. |
| 7,898,288 B2 | 3/2011 | Wong |
| 7,900,805 B2 | 3/2011 | Shelton, IV et al. |
| 7,901,398 B2 | 3/2011 | Stanczak et al. |
| 7,901,400 B2 | 3/2011 | Wham et al. |
| 7,905,380 B2 | 3/2011 | Shelton, IV et al. |
| 7,905,881 B2 | 3/2011 | Masuda et al. |
| 7,909,820 B2 | 3/2011 | Lipson et al. |
| 7,909,823 B2 | 3/2011 | Moses et al. |
| 7,909,824 B2 | 3/2011 | Masuda et al. |
| 7,918,848 B2 | 4/2011 | Lau et al. |
| 7,922,718 B2 | 4/2011 | Moses et al. |
| 7,922,742 B2 | 4/2011 | Hillstead et al. |
| 7,922,953 B2 | 4/2011 | Guerra |
| 7,931,649 B2 | 4/2011 | Couture et al. |
| 7,935,052 B2 | 5/2011 | Dumbauld |
| 7,945,332 B2 | 5/2011 | Schechter |
| 7,947,041 B2 | 5/2011 | Tetzlaff et al. |
| 7,949,407 B2 | 5/2011 | Kaplan et al. |
| 7,951,149 B2 | 5/2011 | Carlton |
| 7,951,150 B2 | 5/2011 | Johnson et al. |
| 7,955,326 B2 | 6/2011 | Paul et al. |
| 7,955,327 B2 | 6/2011 | Sartor et al. |
| 7,955,331 B2 | 6/2011 | Truckai et al. |
| 7,955,332 B2 | 6/2011 | Arts et al. |
| 7,963,965 B2 | 6/2011 | Buysse et al. |
| 7,967,839 B2 | 6/2011 | Flock et al. |
| 7,972,328 B2 | 7/2011 | Wham et al. |
| 7,972,331 B2 | 7/2011 | Hafner |
| 7,976,544 B2 | 7/2011 | McClurken et al. |
| 7,981,113 B2 | 7/2011 | Truckai et al. |
| 7,988,507 B2 | 8/2011 | Darley et al. |
| 7,998,095 B2 | 8/2011 | McAuley |
| 8,012,150 B2 | 9/2011 | Wham et al. |
| 8,016,827 B2 | 9/2011 | Chojin |
| 8,034,049 B2 | 10/2011 | Odom et al. |
| D649,249 S | 11/2011 | Guerra |
| D649,643 S | 11/2011 | Allen, IV et al. |
| 8,048,074 B2 | 11/2011 | Masuda |
| 8,070,746 B2 | 12/2011 | Orton et al. |
| 8,070,748 B2 | 12/2011 | Hixson et al. |
| 8,075,580 B2 | 12/2011 | Makower |
| 8,089,417 B2 | 1/2012 | Popovic et al. |
| 8,092,451 B2 | 1/2012 | Schechter et al. |
| 8,104,956 B2 | 1/2012 | Blaha |
| 8,112,871 B2 | 2/2012 | Brandt et al. |
| 8,114,122 B2 | 2/2012 | Nau, Jr. |
| 8,123,743 B2 | 2/2012 | Arts et al. |
| 8,128,624 B2 | 3/2012 | Couture et al. |
| 8,128,625 B2 | 3/2012 | Odom |
| 8,133,224 B2 | 3/2012 | Geiselhart |
| 8,133,254 B2 | 3/2012 | Dumbauld et al. |
| 8,147,489 B2 | 4/2012 | Moses et al. |
| 8,192,433 B2 | 6/2012 | Johnson et al. |
| 8,241,282 B2 | 8/2012 | Unger et al. |
| 8,333,765 B2 | 12/2012 | Johnson et al. |
| 8,454,602 B2 | 6/2013 | Kerr et al. |
| 8,512,371 B2 | 8/2013 | Kerr et al. |
| 8,523,898 B2 | 9/2013 | Bucciaglia et al. |

(56) References Cited

U.S. PATENT DOCUMENTS

| | | |
|---|---|---|
| 8,529,566 B2 | 9/2013 | Kappus et al. |
| 8,568,408 B2 | 10/2013 | Townsend et al. |
| 8,568,412 B2 | 10/2013 | Brandt et al. |
| 8,591,510 B2 | 11/2013 | Allen, IV et al. |
| 8,628,557 B2 | 1/2014 | Collings et al. |
| 8,668,689 B2 | 3/2014 | Dumbauld et al. |
| 8,679,098 B2 | 3/2014 | Hart |
| 8,679,114 B2 | 3/2014 | Chapman et al. |
| 8,679,115 B2 | 3/2014 | Reschke |
| 8,679,140 B2 | 3/2014 | Butcher |
| 8,685,009 B2 | 4/2014 | Chernov et al. |
| 8,685,056 B2 | 4/2014 | Evans et al. |
| 8,696,667 B2 | 4/2014 | Guerra et al. |
| 8,702,737 B2 | 4/2014 | Chojin et al. |
| 8,702,749 B2 | 4/2014 | Twomey |
| 8,745,840 B2 | 6/2014 | Hempstead et al. |
| 8,747,413 B2 | 6/2014 | Dycus |
| 8,747,434 B2 | 6/2014 | Larson et al. |
| 8,752,264 B2 | 6/2014 | Ackley et al. |
| 8,756,785 B2 | 6/2014 | Allen, IV et al. |
| 8,777,945 B2 | 7/2014 | Floume et al. |
| 8,845,636 B2 | 9/2014 | Allen, IV et al. |
| 8,852,185 B2 | 10/2014 | Twomey |
| 8,864,753 B2 | 10/2014 | Nau, Jr. et al. |
| 8,864,795 B2 | 10/2014 | Kerr et al. |
| 8,887,373 B2 | 11/2014 | Brandt et al. |
| 8,888,771 B2 | 11/2014 | Twomey |
| 8,900,232 B2 | 12/2014 | Ourada |
| 8,920,461 B2 | 12/2014 | Unger et al. |
| 8,939,972 B2 | 1/2015 | Twomey |
| 8,961,313 B2 | 2/2015 | Zalewski |
| 8,961,514 B2 | 2/2015 | Garrison |
| 8,961,515 B2 | 2/2015 | Twomey et al. |
| 8,967,305 B2 | 3/2015 | Manganaro |
| 8,968,283 B2 | 3/2015 | Kharin |
| 8,968,298 B2 | 3/2015 | Twomey |
| 8,968,306 B2 | 3/2015 | Unger |
| 8,968,307 B2 | 3/2015 | Evans et al. |
| 8,968,308 B2 | 3/2015 | Homer et al. |
| 8,968,309 B2 | 3/2015 | Roy et al. |
| 8,968,310 B2 | 3/2015 | Twomey et al. |
| 8,968,311 B2 | 3/2015 | Allen, IV et al. |
| 8,968,317 B2 | 3/2015 | Evans et al. |
| 8,968,360 B2 | 3/2015 | Garrison et al. |
| 9,011,435 B2 | 4/2015 | Brandt et al. |
| 9,023,035 B2 | 5/2015 | Allen, IV et al. |
| 9,024,237 B2 | 5/2015 | Bonn |
| 9,028,492 B2 | 5/2015 | Kerr et al. |
| 9,028,493 B2 | 5/2015 | Dumbauld et al. |
| 9,033,981 B2 | 5/2015 | Olson et al. |
| 9,034,009 B2 | 5/2015 | Twomey et al. |
| 9,039,691 B2 | 5/2015 | Moua et al. |
| 9,039,704 B2 | 5/2015 | Joseph |
| 9,039,732 B2 | 5/2015 | Sims et al. |
| 9,060,780 B2 | 6/2015 | Twomey et al. |
| 9,060,798 B2 | 6/2015 | Harper et al. |
| 9,072,524 B2 | 7/2015 | Heard et al. |
| 9,113,882 B2 | 8/2015 | Twomey et al. |
| 9,113,899 B2 | 8/2015 | Garrison et al. |
| 9,113,901 B2 | 8/2015 | Allen, IV et al. |
| 9,113,909 B2 | 8/2015 | Twomey et al. |
| 9,113,933 B2 | 8/2015 | Chernova et al. |
| 9,113,934 B2 | 8/2015 | Chernov et al. |
| 9,113,938 B2 | 8/2015 | Kerr |
| 9,161,807 B2 | 10/2015 | Garrison |
| 2002/0107517 A1 | 8/2002 | Witt et al. |
| 2002/0111624 A1 | 8/2002 | Witt et al. |
| 2002/0165469 A1 | 11/2002 | Murakami |
| 2003/0014052 A1 | 1/2003 | Buysse et al. |
| 2003/0014053 A1 | 1/2003 | Nguyen et al. |
| 2003/0018332 A1 | 1/2003 | Schmaltz et al. |
| 2003/0069570 A1 | 4/2003 | Witzel et al. |
| 2003/0109875 A1 | 6/2003 | Tetzlaff et al. |
| 2003/0114851 A1 | 6/2003 | Truckai et al. |
| 2003/0130653 A1 | 7/2003 | Sixto et al. |
| 2003/0139741 A1 | 7/2003 | Goble et al. |
| 2003/0158548 A1 | 8/2003 | Phan et al. |
| 2003/0171747 A1 | 9/2003 | Kanehira et al. |
| 2003/0181910 A1 | 9/2003 | Dycus et al. |
| 2003/0191396 A1 | 10/2003 | Sanghvi et al. |
| 2003/0216732 A1 | 11/2003 | Truckai et al. |
| 2003/0229344 A1 | 12/2003 | Dycus et al. |
| 2003/0236325 A1 | 12/2003 | Bonora |
| 2004/0030330 A1 | 2/2004 | Brassell et al. |
| 2004/0064151 A1 | 4/2004 | Mollenauer |
| 2004/0073238 A1 | 4/2004 | Makower |
| 2004/0073256 A1 | 4/2004 | Marchitto et al. |
| 2004/0115296 A1 | 6/2004 | Duffin |
| 2004/0176779 A1 | 9/2004 | Casutt et al. |
| 2004/0199181 A1 | 10/2004 | Knodel et al. |
| 2004/0224590 A1 | 11/2004 | Rawa et al. |
| 2004/0236326 A1 | 11/2004 | Schulze et al. |
| 2004/0249374 A1 | 12/2004 | Tetzlaff et al. |
| 2004/0260281 A1 | 12/2004 | Baxter et al. |
| 2005/0004564 A1 | 1/2005 | Wham et al. |
| 2005/0004569 A1 | 1/2005 | Witt et al. |
| 2005/0033278 A1 | 2/2005 | McClurken et al. |
| 2005/0059858 A1 | 3/2005 | Frith et al. |
| 2005/0059934 A1 | 3/2005 | Wenchell et al. |
| 2005/0090817 A1 | 4/2005 | Phan |
| 2005/0096645 A1 | 5/2005 | Wellman et al. |
| 2005/0149017 A1 | 7/2005 | Dycus |
| 2005/0254081 A1 | 11/2005 | Ryu et al. |
| 2005/0283148 A1 | 12/2005 | Janssen et al. |
| 2006/0052779 A1 | 3/2006 | Hammill |
| 2006/0064086 A1 | 3/2006 | Odom |
| 2006/0079933 A1 | 4/2006 | Hushka et al. |
| 2006/0084973 A1 | 4/2006 | Hushka |
| 2006/0111711 A1 | 5/2006 | Goble |
| 2006/0173452 A1 | 8/2006 | Buysse et al. |
| 2006/0190035 A1 | 8/2006 | Hushka et al. |
| 2006/0217709 A1 | 9/2006 | Couture et al. |
| 2006/0224053 A1 | 10/2006 | Black et al. |
| 2006/0253126 A1 | 11/2006 | Bjerken et al. |
| 2006/0259036 A1 | 11/2006 | Tetzlaff et al. |
| 2006/0264922 A1 | 11/2006 | Sartor et al. |
| 2006/0271030 A1 | 11/2006 | Francis et al. |
| 2006/0283093 A1 | 12/2006 | Petrovic et al. |
| 2006/0287641 A1 | 12/2006 | Perlin |
| 2007/0027447 A1 | 2/2007 | Theroux et al. |
| 2007/0043337 A1 | 2/2007 | McAuley |
| 2007/0043353 A1 | 2/2007 | Dycus et al. |
| 2007/0062017 A1 | 3/2007 | Dycus et al. |
| 2007/0118115 A1 | 5/2007 | Artale et al. |
| 2007/0173811 A1 | 7/2007 | Couture et al. |
| 2007/0173813 A1 | 7/2007 | Odom |
| 2007/0198011 A1 | 8/2007 | Sugita |
| 2007/0225695 A1 | 9/2007 | Mayer et al. |
| 2007/0255279 A1 | 11/2007 | Buysse et al. |
| 2007/0260238 A1 | 11/2007 | Guerra |
| 2007/0260242 A1 | 11/2007 | Dycus et al. |
| 2007/0265616 A1 | 11/2007 | Couture et al. |
| 2007/0265620 A1 | 11/2007 | Kraas et al. |
| 2008/0004616 A1 | 1/2008 | Patrick |
| 2008/0004656 A1* | 1/2008 | Livneh ............... A61B 17/29 606/205 |
| 2008/0015575 A1 | 1/2008 | Odom et al. |
| 2008/0033428 A1 | 1/2008 | Artale et al. |
| 2008/0039831 A1 | 2/2008 | Odom et al. |
| 2008/0039835 A1 | 2/2008 | Johnson et al. |
| 2008/0046122 A1 | 2/2008 | Manzo et al. |
| 2008/0058802 A1 | 3/2008 | Couture et al. |
| 2008/0082100 A1 | 4/2008 | Orton et al. |
| 2008/0125767 A1 | 5/2008 | Blaha |
| 2008/0125797 A1 | 5/2008 | Kelleher |
| 2008/0171938 A1 | 7/2008 | Masuda et al. |
| 2008/0172051 A1 | 7/2008 | Masuda et al. |
| 2008/0208289 A1 | 8/2008 | Darley et al. |
| 2008/0215050 A1 | 9/2008 | Bakos |
| 2008/0234701 A1 | 9/2008 | Morales et al. |
| 2008/0243106 A1 | 10/2008 | Coe et al. |
| 2008/0243120 A1 | 10/2008 | Lawes et al. |
| 2008/0243158 A1 | 10/2008 | Morgan |
| 2008/0249523 A1 | 10/2008 | McPherson et al. |

(56) References Cited

U.S. PATENT DOCUMENTS

| | | |
|---|---|---|
| 2008/0249527 A1 | 10/2008 | Couture |
| 2008/0271360 A1 | 11/2008 | Barfield |
| 2008/0281311 A1 | 11/2008 | Dunning et al. |
| 2008/0300580 A1 | 12/2008 | Shelton, IV et al. |
| 2008/0312653 A1 | 12/2008 | Arts et al. |
| 2008/0319292 A1 | 12/2008 | Say et al. |
| 2009/0012520 A1 | 1/2009 | Hixson et al. |
| 2009/0012556 A1 | 1/2009 | Boudreaux et al. |
| 2009/0015832 A1 | 1/2009 | Popovic et al. |
| 2009/0024126 A1 | 1/2009 | Artale et al. |
| 2009/0036881 A1 | 2/2009 | Artale et al. |
| 2009/0036899 A1 | 2/2009 | Carlton et al. |
| 2009/0043304 A1 | 2/2009 | Tetzlaff et al. |
| 2009/0048596 A1 | 2/2009 | Shields et al. |
| 2009/0054894 A1 | 2/2009 | Yachi |
| 2009/0062794 A1 | 3/2009 | Buysse et al. |
| 2009/0065565 A1 | 3/2009 | Cao |
| 2009/0076506 A1 | 3/2009 | Baker |
| 2009/0076534 A1 | 3/2009 | Shelton, IV et al. |
| 2009/0082766 A1 | 3/2009 | Unger et al. |
| 2009/0088738 A1 | 4/2009 | Guerra et al. |
| 2009/0088739 A1 | 4/2009 | Hushka et al. |
| 2009/0088740 A1 | 4/2009 | Guerra et al. |
| 2009/0088741 A1 | 4/2009 | Hushka et al. |
| 2009/0088744 A1 | 4/2009 | Townsend |
| 2009/0088745 A1 | 4/2009 | Hushka et al. |
| 2009/0088746 A1 | 4/2009 | Hushka et al. |
| 2009/0088747 A1 | 4/2009 | Hushka et al. |
| 2009/0088748 A1 | 4/2009 | Guerra et al. |
| 2009/0088749 A1 | 4/2009 | Hushka et al. |
| 2009/0088750 A1 | 4/2009 | Hushka et al. |
| 2009/0105750 A1 | 4/2009 | Price et al. |
| 2009/0112200 A1 | 4/2009 | Eggers |
| 2009/0112206 A1 | 4/2009 | Dumbauld et al. |
| 2009/0112229 A1 | 4/2009 | Omori et al. |
| 2009/0131934 A1 | 5/2009 | Odom et al. |
| 2009/0138006 A1 | 5/2009 | Bales et al. |
| 2009/0149853 A1 | 6/2009 | Shields et al. |
| 2009/0149854 A1 | 6/2009 | Cunningham et al. |
| 2009/0157071 A1 | 6/2009 | Wham et al. |
| 2009/0157072 A1 | 6/2009 | Wham et al. |
| 2009/0157075 A1 | 6/2009 | Wham et al. |
| 2009/0171350 A1 | 7/2009 | Dycus et al. |
| 2009/0171354 A1 | 7/2009 | Deville et al. |
| 2009/0177094 A1 | 7/2009 | Brown et al. |
| 2009/0182327 A1 | 7/2009 | Unger |
| 2009/0182329 A1 | 7/2009 | Dycus |
| 2009/0187188 A1 | 7/2009 | Guerra et al. |
| 2009/0198233 A1 | 8/2009 | Chojin |
| 2009/0204114 A1 | 8/2009 | Odom |
| 2009/0204137 A1 | 8/2009 | Maxwell |
| 2009/0206126 A1 | 8/2009 | Huitema et al. |
| 2009/0209957 A1 | 8/2009 | Schmaltz et al. |
| 2009/0209960 A1 | 8/2009 | Chojin |
| 2009/0234354 A1 | 9/2009 | Johnson et al. |
| 2009/0248007 A1 | 10/2009 | Falkenstein et al. |
| 2009/0248013 A1 | 10/2009 | Falkenstein et al. |
| 2009/0248019 A1 | 10/2009 | Falkenstein et al. |
| 2009/0248020 A1 | 10/2009 | Falkenstein et al. |
| 2009/0248021 A1 | 10/2009 | McKenna |
| 2009/0248022 A1 | 10/2009 | Falkenstein et al. |
| 2009/0248050 A1 | 10/2009 | Hirai |
| 2009/0248051 A1 | 10/2009 | Masuda |
| 2009/0254080 A1 | 10/2009 | Honda |
| 2009/0254081 A1 | 10/2009 | Allison et al. |
| 2009/0261804 A1 | 10/2009 | McKenna et al. |
| 2009/0270771 A1 | 10/2009 | Takahashi |
| 2009/0292282 A9 | 11/2009 | Dycus |
| 2009/0318912 A1 | 12/2009 | Mayer et al. |
| 2010/0016857 A1 | 1/2010 | McKenna et al. |
| 2010/0023009 A1 | 1/2010 | Moses et al. |
| 2010/0030028 A1 | 2/2010 | Cabrera et al. |
| 2010/0036375 A1 | 2/2010 | Regadas |
| 2010/0042140 A1 | 2/2010 | Cunningham |
| 2010/0042142 A1 | 2/2010 | Cunningham |
| 2010/0042143 A1 | 2/2010 | Cunningham |
| 2010/0049187 A1 | 2/2010 | Carlton et al. |
| 2010/0049194 A1 | 2/2010 | Hart et al. |
| 2010/0057078 A1 | 3/2010 | Arts et al. |
| 2010/0057081 A1 | 3/2010 | Hanna |
| 2010/0057082 A1 | 3/2010 | Hanna |
| 2010/0057083 A1 | 3/2010 | Hanna |
| 2010/0057084 A1 | 3/2010 | Hanna |
| 2010/0063500 A1 | 3/2010 | Muszala |
| 2010/0069903 A1 | 3/2010 | Allen, IV et al. |
| 2010/0069904 A1 | 3/2010 | Cunningham |
| 2010/0069953 A1 | 3/2010 | Cunningham et al. |
| 2010/0076427 A1 | 3/2010 | Heard |
| 2010/0076430 A1 | 3/2010 | Romero |
| 2010/0076431 A1 | 3/2010 | Allen, IV |
| 2010/0076432 A1 | 3/2010 | Horner |
| 2010/0087816 A1 | 4/2010 | Roy |
| 2010/0087818 A1 | 4/2010 | Cunningham |
| 2010/0094271 A1 | 4/2010 | Ward et al. |
| 2010/0094286 A1 | 4/2010 | Chojin |
| 2010/0094287 A1 | 4/2010 | Cunningham et al. |
| 2010/0094289 A1 | 4/2010 | Taylor et al. |
| 2010/0100122 A1 | 4/2010 | Hinton |
| 2010/0130971 A1 | 5/2010 | Baily |
| 2010/0130977 A1 | 5/2010 | Garrison et al. |
| 2010/0145334 A1 | 6/2010 | Olson et al. |
| 2010/0179539 A1 | 7/2010 | Nau, Jr. |
| 2010/0179543 A1 | 7/2010 | Johnson et al. |
| 2010/0179545 A1 | 7/2010 | Twomey et al. |
| 2010/0179546 A1 | 7/2010 | Cunningham |
| 2010/0179547 A1 | 7/2010 | Cunningham et al. |
| 2010/0198215 A1 | 8/2010 | Julian et al. |
| 2010/0198218 A1 | 8/2010 | Manzo |
| 2010/0198248 A1 | 8/2010 | Vakharia |
| 2010/0217264 A1 | 8/2010 | Odom et al. |
| 2010/0228249 A1 | 9/2010 | Mohr et al. |
| 2010/0228250 A1 | 9/2010 | Brogna |
| 2010/0249769 A1 | 9/2010 | Nau, Jr. et al. |
| 2010/0249776 A1 | 9/2010 | Kerr |
| 2010/0256635 A1 | 10/2010 | McKenna et al. |
| 2010/0274160 A1 | 10/2010 | Yachi et al. |
| 2010/0274244 A1 | 10/2010 | Heard |
| 2010/0274265 A1 | 10/2010 | Wingardner et al. |
| 2010/0280511 A1 | 11/2010 | Rachlin et al. |
| 2010/0280515 A1 | 11/2010 | Hixson et al. |
| 2010/0286691 A1 | 11/2010 | Kerr et al. |
| 2010/0292691 A1 | 11/2010 | Brogna |
| 2010/0307934 A1 | 12/2010 | Chowaniec et al. |
| 2010/0312235 A1 | 12/2010 | Bahney |
| 2010/0312238 A1 | 12/2010 | Schechter et al. |
| 2010/0312242 A1 | 12/2010 | Odom |
| 2010/0331742 A1 | 12/2010 | Masuda |
| 2010/0331839 A1 | 12/2010 | Schechter et al. |
| 2011/0004209 A1 | 1/2011 | Lawes et al. |
| 2011/0004210 A1 | 1/2011 | Johnson et al. |
| 2011/0009864 A1 | 1/2011 | Bucciaglia et al. |
| 2011/0015632 A1 | 1/2011 | Artale |
| 2011/0018164 A1 | 1/2011 | Sartor et al. |
| 2011/0034918 A1 | 2/2011 | Reschke |
| 2011/0036183 A1 | 2/2011 | Artale et al. |
| 2011/0054467 A1 | 3/2011 | Mueller et al. |
| 2011/0054468 A1 | 3/2011 | Dycus |
| 2011/0054469 A1 | 3/2011 | Kappus et al. |
| 2011/0054471 A1 | 3/2011 | Gerhardt et al. |
| 2011/0054472 A1 | 3/2011 | Romero |
| 2011/0060333 A1 | 3/2011 | Mueller |
| 2011/0060335 A1 | 3/2011 | Harper et al. |
| 2011/0060356 A1 | 3/2011 | Reschke et al. |
| 2011/0066174 A1 | 3/2011 | Gilbert |
| 2011/0071522 A1 | 3/2011 | Dumbauld et al. |
| 2011/0071523 A1 | 3/2011 | Dickhans |
| 2011/0071525 A1 | 3/2011 | Dumbauld et al. |
| 2011/0072638 A1 | 3/2011 | Brandt et al. |
| 2011/0073246 A1 | 3/2011 | Brandt et al. |
| 2011/0077649 A1 | 3/2011 | Kingsley |
| 2011/0082457 A1 | 4/2011 | Kerr et al. |
| 2011/0087221 A1 | 4/2011 | Siebrecht et al. |
| 2011/0098689 A1 | 4/2011 | Nau, Jr. et al. |
| 2011/0106079 A1 | 5/2011 | Garrison et al. |

(56) References Cited

U.S. PATENT DOCUMENTS

| | | |
|---|---|---|
| 2011/0162796 A1 | 7/2011 | Guerra |
| 2011/0178519 A1 | 7/2011 | Couture et al. |
| 2011/0184405 A1 | 7/2011 | Mueller |
| 2011/0190653 A1 | 8/2011 | Harper et al. |
| 2011/0190765 A1 | 8/2011 | Chojin |
| 2011/0193608 A1 | 8/2011 | Krapohl |
| 2011/0218530 A1 | 9/2011 | Reschke |
| 2011/0230880 A1 | 9/2011 | Chojin et al. |
| 2011/0238066 A1 | 9/2011 | Olson |
| 2011/0238067 A1 | 9/2011 | Moses et al. |
| 2011/0251605 A1 | 10/2011 | Hoarau et al. |
| 2011/0251606 A1 | 10/2011 | Kerr |
| 2011/0251611 A1 | 10/2011 | Horner et al. |
| 2011/0270245 A1 | 11/2011 | Horner et al. |
| 2011/0270250 A1 | 11/2011 | Horner et al. |
| 2011/0270251 A1 | 11/2011 | Horner et al. |
| 2011/0270252 A1 | 11/2011 | Horner et al. |
| 2011/0276048 A1 | 11/2011 | Kerr et al. |
| 2011/0276049 A1 | 11/2011 | Gerhardt |
| 2011/0295251 A1 | 12/2011 | Garrison |
| 2011/0295313 A1 | 12/2011 | Kerr |
| 2011/0301592 A1 | 12/2011 | Kerr et al. |
| 2011/0301599 A1 | 12/2011 | Roy et al. |
| 2011/0301600 A1 | 12/2011 | Garrison et al. |
| 2011/0301601 A1 | 12/2011 | Garrison et al. |
| 2011/0301602 A1 | 12/2011 | Roy et al. |
| 2011/0301603 A1 | 12/2011 | Kerr et al. |
| 2011/0301604 A1 | 12/2011 | Horner et al. |
| 2011/0301605 A1 | 12/2011 | Homer |
| 2011/0301606 A1 | 12/2011 | Kerr |
| 2011/0301637 A1 | 12/2011 | Kerr et al. |
| 2011/0319886 A1 | 12/2011 | Chojin et al. |
| 2011/0319888 A1 | 12/2011 | Mueller et al. |
| 2012/0004658 A1 | 1/2012 | Chojin |
| 2012/0010614 A1 | 1/2012 | Couture |
| 2012/0022532 A1 | 1/2012 | Garrison |
| 2012/0029515 A1 | 2/2012 | Couture |
| 2012/0041438 A1 | 2/2012 | Nau, Jr. et al. |
| 2012/0046659 A1 | 2/2012 | Mueller |
| 2012/0046660 A1 | 2/2012 | Nau, Jr. |
| 2012/0046662 A1 | 2/2012 | Gilbert |
| 2012/0059371 A1 | 3/2012 | Anderson et al. |
| 2012/0059372 A1 | 3/2012 | Johnson |
| 2012/0059374 A1 | 3/2012 | Johnson et al. |
| 2012/0059375 A1 | 3/2012 | Couture et al. |
| 2012/0059408 A1 | 3/2012 | Mueller |
| 2012/0059409 A1 | 3/2012 | Reschke et al. |
| 2012/0078250 A1 | 3/2012 | Orton et al. |
| 2012/0083785 A1 | 4/2012 | Roy et al. |
| 2012/0083786 A1 | 4/2012 | Artale et al. |
| 2012/0083827 A1 | 4/2012 | Artale et al. |
| 2012/0095456 A1 | 4/2012 | Schechter et al. |
| 2012/0095460 A1 | 4/2012 | Rooks et al. |
| 2012/0239034 A1 | 9/2012 | Homer et al. |
| 2012/0259331 A1 | 10/2012 | Garrison |
| 2012/0265241 A1 | 10/2012 | Hart et al. |
| 2012/0296205 A1 | 11/2012 | Chernov et al. |
| 2012/0296238 A1 | 11/2012 | Chernov et al. |
| 2012/0296239 A1 | 11/2012 | Chernov et al. |
| 2012/0296323 A1 | 11/2012 | Chernov et al. |
| 2012/0296371 A1 | 11/2012 | Kappus et al. |
| 2012/0303026 A1 | 11/2012 | Dycus et al. |
| 2012/0323238 A1 | 12/2012 | Tyrrell et al. |
| 2012/0330308 A1 | 12/2012 | Joseph |
| 2013/0018364 A1 | 1/2013 | Chernov et al. |
| 2013/0022495 A1 | 1/2013 | Allen, IV et al. |
| 2013/0071282 A1 | 3/2013 | Fry |
| 2013/0072927 A1 | 3/2013 | Allen, IV et al. |
| 2013/0079760 A1 | 3/2013 | Twomey et al. |
| 2013/0079774 A1 | 3/2013 | Whitney et al. |
| 2013/0085496 A1 | 4/2013 | Unger et al. |
| 2013/0103030 A1 | 4/2013 | Garrison |
| 2013/0103031 A1 | 4/2013 | Garrison |
| 2013/0138101 A1 | 5/2013 | Kerr |
| 2013/0144284 A1 | 6/2013 | Behnke, II et al. |
| 2013/0197503 A1 | 8/2013 | Orszulak |
| 2013/0253489 A1 | 9/2013 | Nau, Jr. et al. |
| 2013/0255063 A1 | 10/2013 | Hart et al. |
| 2013/0274736 A1 | 10/2013 | Garrison |
| 2013/0289561 A1 | 10/2013 | Waaler et al. |
| 2013/0296922 A1 | 11/2013 | Allen, IV et al. |
| 2013/0304058 A1 | 11/2013 | Kendrick |
| 2013/0304066 A1 | 11/2013 | Kerr et al. |
| 2013/0325057 A1 | 12/2013 | Larson et al. |

FOREIGN PATENT DOCUMENTS

| | | |
|---|---|---|
| CA | 2590520 A1 | 11/2007 |
| CN | 201299462 | 9/2009 |
| DE | 2415263 A1 | 10/1975 |
| DE | 02514501 A1 | 10/1976 |
| DE | 2627679 A1 | 1/1977 |
| DE | 03423356 C2 | 6/1986 |
| DE | 03612646 A1 | 4/1987 |
| DE | 8712328 U1 | 2/1988 |
| DE | 04303882 C2 | 2/1995 |
| DE | 04403252 A1 | 8/1995 |
| DE | 19515914 C1 | 7/1996 |
| DE | 19506363 A1 | 8/1996 |
| DE | 29616210 U1 | 11/1996 |
| DE | 19608716 C1 | 4/1997 |
| DE | 19751106 A1 | 5/1998 |
| DE | 19751108 A1 | 5/1999 |
| DE | 19946527 C1 | 7/2001 |
| DE | 10045375 C2 | 10/2002 |
| DE | 202007009165 U1 | 8/2007 |
| DE | 202007009317 U1 | 8/2007 |
| DE | 202007016233 U1 | 1/2008 |
| DE | 19738457 B4 | 1/2009 |
| DE | 102004026179 B4 | 1/2009 |
| DE | 102008018406 B3 | 7/2009 |
| EP | 0467501 A1 | 1/1992 |
| EP | 0509670 A3 | 12/1992 |
| EP | 0306123 B1 | 8/1993 |
| EP | 0572131 A1 | 12/1993 |
| EP | 0584787 A1 | 3/1994 |
| EP | 0589555 A1 | 3/1994 |
| EP | 0589453 A3 | 4/1994 |
| EP | 0648475 A1 | 4/1995 |
| EP | 0624348 A3 | 6/1995 |
| EP | 0364216 B1 | 1/1996 |
| EP | 0518230 B1 | 5/1996 |
| EP | 0517243 B1 | 9/1997 |
| EP | 0541930 B1 | 3/1998 |
| EP | 0878169 A1 | 11/1998 |
| EP | 0623316 B1 | 3/1999 |
| EP | 0650701 B1 | 3/1999 |
| EP | 0923907 A1 | 6/1999 |
| EP | 0640317 B1 | 9/1999 |
| EP | 0950378 A1 | 10/1999 |
| EP | 0986990 A1 | 3/2000 |
| EP | 1034747 A1 | 9/2000 |
| EP | 1034748 | 9/2000 |
| EP | 0694290 B1 | 11/2000 |
| EP | 1050278 | 11/2000 |
| EP | 1053719 | 11/2000 |
| EP | 1053720 | 11/2000 |
| EP | 1055399 | 11/2000 |
| EP | 1055400 | 11/2000 |
| EP | 1080694 | 3/2001 |
| EP | 1082944 | 3/2001 |
| EP | 1177771 | 2/2002 |
| EP | 1278007 A1 | 1/2003 |
| EP | 1159926 A3 | 3/2003 |
| EP | 0717966 B1 | 4/2003 |
| EP | 1301135 | 4/2003 |
| EP | 0887046 B1 | 7/2003 |
| EP | 1330991 A1 | 7/2003 |
| EP | 1486177 | 6/2004 |
| EP | 0913126 B1 | 10/2004 |
| EP | 1472984 | 11/2004 |
| EP | 0754437 B2 | 12/2004 |
| EP | 0888747 B1 | 12/2004 |
| EP | 1025807 B1 | 12/2004 |

(56) References Cited

FOREIGN PATENT DOCUMENTS

| | | |
|---|---|---|
| EP | 0774232 B1 | 1/2005 |
| EP | 0853922 B1 | 2/2005 |
| EP | 1527747 | 5/2005 |
| EP | 1530952 | 5/2005 |
| EP | 1532932 A1 | 5/2005 |
| EP | 1535581 | 6/2005 |
| EP | 1545360 A1 | 6/2005 |
| EP | 1609430 | 12/2005 |
| EP | 1201192 | 2/2006 |
| EP | 1034746 B1 | 3/2006 |
| EP | 1632192 | 3/2006 |
| EP | 1186274 | 4/2006 |
| EP | 1642543 | 4/2006 |
| EP | 1645238 A1 | 4/2006 |
| EP | 1645240 A2 | 4/2006 |
| EP | 1649821 | 4/2006 |
| EP | 0875209 B1 | 5/2006 |
| EP | 1707143 A1 | 10/2006 |
| EP | 1767163 A1 | 3/2007 |
| EP | 1769765 A1 | 4/2007 |
| EP | 1769766 | 4/2007 |
| EP | 1772109 | 4/2007 |
| EP | 1785097 | 5/2007 |
| EP | 1785098 | 5/2007 |
| EP | 1785101 | 5/2007 |
| EP | 1787597 | 5/2007 |
| EP | 1810625 A1 | 7/2007 |
| EP | 1810628 A1 | 7/2007 |
| EP | 1842500 | 10/2007 |
| EP | 1878400 | 1/2008 |
| EP | 1894535 | 3/2008 |
| EP | 1929970 | 6/2008 |
| EP | 1946715 | 7/2008 |
| EP | 1958583 A2 | 8/2008 |
| EP | 1990019 | 11/2008 |
| EP | 1683496 | 12/2008 |
| EP | 1997438 | 12/2008 |
| EP | 1997439 | 12/2008 |
| EP | 1527744 | 2/2009 |
| EP | 2103268 | 9/2009 |
| EP | 2105104 | 9/2009 |
| EP | 2147649 | 1/2010 |
| EP | 2153791 | 2/2010 |
| EP | 2206474 | 7/2010 |
| EP | 1920725 | 10/2010 |
| EP | 2243439 | 10/2010 |
| EP | 2294998 | 3/2011 |
| EP | 2301467 | 3/2011 |
| EP | 1628586 | 7/2011 |
| GB | 623316 | 5/1949 |
| GB | 1490585 | 11/1977 |
| GB | 2213416 A | 8/1989 |
| GB | 2214430 A | 9/1989 |
| JP | 61-501068 | 9/1984 |
| JP | 10-24051 A | 1/1989 |
| JP | 11-47150 A | 6/1989 |
| JP | 6-502328 | 3/1992 |
| JP | 5-5106 | 1/1993 |
| JP | 05-40112 | 2/1993 |
| JP | 0006030945 A | 2/1994 |
| JP | 6-121797 A | 5/1994 |
| JP | 6-285078 A | 10/1994 |
| JP | 6-511401 | 12/1994 |
| JP | 06343644 A | 12/1994 |
| JP | 07265328 A | 10/1995 |
| JP | 8-56955 | 5/1996 |
| JP | 08252263 A | 10/1996 |
| JP | 8-289895 A | 11/1996 |
| JP | 8-317934 A | 12/1996 |
| JP | 8-317936 A | 12/1996 |
| JP | 9-10223 C | 1/1997 |
| JP | 9-122138 A | 5/1997 |
| JP | 10-155798 A | 6/1998 |
| JP | 11-070124 A | 3/1999 |
| JP | 11-169381 A | 6/1999 |
| JP | 11-192238 A | 7/1999 |
| JP | 11244298 A | 9/1999 |
| JP | 2000-102545 A | 4/2000 |
| JP | 2000342599 A | 12/2000 |
| JP | 2000350732 A | 12/2000 |
| JP | 2001-8944 | 1/2001 |
| JP | 2001-29356 | 2/2001 |
| JP | 2001128990 A | 5/2001 |
| JP | 2001-190564 A | 7/2001 |
| JP | 2001-3400 | 11/2001 |
| JP | 2002-528166 A | 9/2002 |
| JP | 2003245285 A | 9/2003 |
| JP | 2004-517668 A | 6/2004 |
| JP | 2004-528869 A | 9/2004 |
| JP | 2011125195 A | 6/2011 |
| SU | 401367 A1 | 10/1973 |
| WO | 89/00757 | 1/1989 |
| WO | 92/04873 | 4/1992 |
| WO | 92/06642 | 4/1992 |
| WO | 93/19681 | 10/1993 |
| WO | 93/21845 | 11/1993 |
| WO | 94/00059 A1 | 1/1994 |
| WO | 94/08524 | 4/1994 |
| WO | 94/20025 | 9/1994 |
| WO | 95/02369 | 1/1995 |
| WO | 95/07662 | 3/1995 |
| WO | 95/15124 | 6/1995 |
| WO | 95/20360 | 8/1995 |
| WO | 95/20921 | 8/1995 |
| WO | 96/05776 | 2/1996 |
| WO | 96/11635 | 4/1996 |
| WO | 96-22056 A1 | 7/1996 |
| WO | 96/13218 | 9/1996 |
| WO | 97/00646 | 1/1997 |
| WO | 97/00647 | 1/1997 |
| WO | 97/10764 | 3/1997 |
| WO | 97/18768 | 5/1997 |
| WO | 97/24073 | 7/1997 |
| WO | 97/24993 | 7/1997 |
| WO | 98/14124 | 4/1998 |
| WO | 98/27880 | 7/1998 |
| WO | 98/31290 | 7/1998 |
| WO | 98/43264 | 10/1998 |
| WO | 99/03407 | 1/1999 |
| WO | 99/03408 | 1/1999 |
| WO | 99/03409 | 1/1999 |
| WO | 99/03414 | 1/1999 |
| WO | 99/12488 | 3/1999 |
| WO | 99-23933 A2 | 5/1999 |
| WO | 99/23959 | 5/1999 |
| WO | 99-25261 A1 | 5/1999 |
| WO | 99/40857 | 8/1999 |
| WO | 99/40861 | 8/1999 |
| WO | 99/51158 | 10/1999 |
| WO | 99/66850 | 12/1999 |
| WO | 00/24322 | 5/2000 |
| WO | 00/24330 | 5/2000 |
| WO | 00/24331 | 5/2000 |
| WO | 00/33753 | 6/2000 |
| WO | 0036986 A1 | 6/2000 |
| WO | 00/41638 | 7/2000 |
| WO | 00/47124 | 8/2000 |
| WO | 00/53112 | 9/2000 |
| WO | 0059392 A1 | 10/2000 |
| WO | 01/01847 | 1/2001 |
| WO | 01/17448 | 3/2001 |
| WO | 0115614 A1 | 3/2001 |
| WO | 0154604 A1 | 8/2001 |
| WO | 01/66025 | 9/2001 |
| WO | 02/07627 | 1/2002 |
| WO | 02/058544 | 8/2002 |
| WO | 02/067798 | 9/2002 |
| WO | 02/080783 | 10/2002 |
| WO | 02/080784 | 10/2002 |
| WO | 02/080785 | 10/2002 |
| WO | 02/080786 | 10/2002 |
| WO | 02/080793 | 10/2002 |
| WO | 02/080794 | 10/2002 |
| WO | 02/080795 | 10/2002 |

(56) References Cited

FOREIGN PATENT DOCUMENTS

| WO | 02/080796 | 10/2002 |
|---|---|---|
| WO | 02/080797 | 10/2002 |
| WO | 02/080798 | 10/2002 |
| WO | 02/080799 A1 | 10/2002 |
| WO | 02/081170 | 10/2002 |
| WO | 02/085218 | 10/2002 |
| WO | 03/061500 | 7/2003 |
| WO | 03/068046 | 8/2003 |
| WO | 03/096880 | 11/2003 |
| WO | 03/101311 | 12/2003 |
| WO | 03/090630 A3 | 4/2004 |
| WO | 2004-028585 A2 | 4/2004 |
| WO | 2004/032776 A1 | 4/2004 |
| WO | 2004/032777 A1 | 4/2004 |
| WO | 2004/052221 A1 | 6/2004 |
| WO | 2004/073488 A2 | 9/2004 |
| WO | 2004/073490 A2 | 9/2004 |
| WO | 2004/073753 A2 | 9/2004 |
| WO | 2004/082495 A1 | 9/2004 |
| WO | 2004/098383 A2 | 11/2004 |
| WO | 2004/103156 A2 | 12/2004 |
| WO | 2005/004734 A1 | 1/2005 |
| WO | 2005/004735 A1 | 1/2005 |
| WO | 2005-009255 A1 | 2/2005 |
| WO | 2005/011049 A2 | 2/2005 |
| WO | 2005/030071 A1 | 4/2005 |
| WO | 2005/048809 A1 | 6/2005 |
| WO | 2005/050151 A1 | 6/2005 |
| WO | 2005/110264 A2 | 11/2005 |
| WO | 2006021269 A1 | 3/2006 |
| WO | 2008/008457 A2 | 1/2008 |
| WO | 2008/045348 A2 | 4/2008 |
| WO | 2008/045350 A2 | 4/2008 |
| WO | 2008040483 A1 | 4/2008 |
| WO | 20080112147 A1 | 9/2008 |
| WO | 20090005850 A1 | 1/2009 |
| WO | 2009032623 A2 | 3/2009 |
| WO | 20090039179 A1 | 3/2009 |
| WO | 20090039510 A1 | 3/2009 |
| WO | 2009124097 A1 | 10/2009 |
| WO | 2010/104753 | 9/2010 |

OTHER PUBLICATIONS

Chung et al., "Clinical Experience of Sutureless Closed Hemorrhoidectomy with LigaSure" Diseases of the Colon & Rectum vol. 46, No. 1 Jan. 2003.

Tinkcler L.F., "Combined Diathermy and Suction Forceps" , Feb. 6, 1967, British Medical Journal Feb. 6, 1976, vol. 1, nr. 5431 p. 361, ISSN: 0007-1447.

Carbonell et al., "Comparison of the Gyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte,NC; Date: Aug. 2003.

Peterson et al. "Comparison of Healing Process Following Ligation with Sutures and Bipolar Vessel Sealing" Surgical Technology International (2001).

"Electrosurgery: A Historical Overview" Innovations in Electrosurgery; Sales/Product Literature; Dec. 31, 2000.

Johnson et al. "Evaluation of a Bipolar Electrothermal Vessel Sealing Device in Hemorrhoidectomy" Sales/Product Literature; Jan. 2004.

E. David Crawford "Evaluation of a New Vessel Sealing Device in Urologic Cancer Surgery" Sales/Product Literature 2000.

Johnson et al. "Evaluation of the LigaSure Vessel Sealing System in Hemorrhoidectormy" American College of Surgeons (ACS) Clinicla Congress Poster (2000).

Muller et al., "Extended Left Hemicolectomy Using the LigaSure Vessel Sealing System" Innovations That Work, Sep. 1999.

Kennedy et al. "High-burst-strength, feedback-controlled bipolar vessel sealing" Surgical Endoscopy (1998) 12: 876-878.

Burdette et al. "In Vivo Probe Measurement Technique for Determining Dielectric Properties at VHF Through Microwave Frequencies", IEEE Transactions on Microwave Theory and Techniques, vol. MTT-28, No. 4, Apr. 1980 pp. 414-427.

Carus et al., "Initial Experience With the LigaSure Vessel Sealing System in Abdominal Surgery", Innovations That Work, Jun. 2002.

Heniford et al. "Initial Research and Clinical Results with an Electrothermal Bipolar Vessel Sealer" Oct. 1999.

Heniford et al. "Initial Results with an Electrothermal Bipolar Vessel Sealer" Surgical Endoscopy (2000) 15:799-801.

Herman et al., "Laparoscopic Intestinal Resection With the LigaSure Vessel Sealing System: A Case Report"; Innovations That Work, Feb. 2002.

Koyle et al., "Laparoscopic Palomo Varicocele Ligation in Children and Adolescents" Pediatric Endosurgery & Innovative Techniques, vol. 6, No. 1, 2002.

W. Scott Helton, "LigaSure Vessel Sealing System: Revolutionary Hemostasis Product for General Surgery"; Sales/Product Literature 1999.

LigaSure Vessel Sealing System, the Seal of Confidence in General, Gynecologic, Urologic, and Laparaoscopic Surgery; Sales/Product Literature; Apr. 2002.

Joseph Ortenberg "LigaSure System Used in Laparoscopic 1st and 2nd Stage Orchiopexy" Innovations That Work, Nov. 2002.

Sigel et al. "The Mechanism of Blood Vessel Closure by High Frequency Electrocoagulation" Surgery Gynecology & Obstetrics, Oct. 1965 pp. 823-831.

Sampayan et al, "Multilayer Ultra-High Gradient Insulator Technology" Discharges and Electrical Insulation in Vacuum, 1998. Netherlands Aug. 17-21, 1998; vol. 2, pp. 740-743.

Paul G. Horgan, "A Novel Technique for Parenchymal Division During Hepatectomy" The American Journal of Surgery, vol. 181, No. 3, Apr. 2001 pp. 236-237.

Benaron et al., "Optical Time-Of-Flight and Absorbance Imaging of Biologic Media", Science, American Association for the Advancement of Science, Washington, DC, vol. 259, Mar. 5, 1993, pp. 1463-1466.

Olsson et al. "Radical Cystectomy in Females" Current Surgical Techniques in Urology, vol. 14, Issue 3, 2001.

Palazzo et al. "Randomized clinical trial of Ligasure versus open haemorrhoidectomy" British Journal of Surgery 2002, 89, 154-157.

Levy et al. "Randomized Trial of Suture Versus Electrosurgical Bipolar Vessel Sealing in Vaginal Hysterectomy" Obstetrics & Gynecology, vol. 102, No. 1, Jul. 2003.

"Reducing Needlestick Injuries in the Operating Room" Sales/Product Literature 2001.

Bergdahl et al. "Studies on Coagulation and the Development of an Automatic Computerized Bipolar Coagulator" J. Neurosurg, vol. 75, Jul. 1991, pp. 148-151.

Strasberg et al. "A Phase I Study of the LigaSure Vessel Sealing System in Hepatic Surgery" Section of HBP Surger, Washington University School of Medicine, St. Louis MO, Presented at AHPBA, Feb. 2001.

Sayfan et al. "Sutureless Closed Hemorrhoidectomy: A New Technique" Annals of Surgery vol. 234 No. 1 Jul. 2001; pp. 21-24.

Levy et al., "Update on Hysterectomy—New Technologies and Techniques" OBG Management, Feb. 2003.

Dulemba et al. "Use of a Bipolar Electrothermal Vessel Sealer in Laparoscopically Assisted Vaginal Hysterectomy" Sales/Product Literature; Jan. 2004.

Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.

Sengupta et al., "Use of a Computer-Controlled Bipolar Diathermy System in Radical Prostatectomies and Other Open Urological Surgery" ANZ Journal of Surgery (2001) 71.9 pp. 538-540.

Rothenberg et al. "Use of the LigaSure Vessel Sealing System in Minimally Invasive Surgery in Children" Int'l Pediatric Endosurgery Group (IPEG) 2000.

Crawford et al. "Use of the LigaSure Vessel Sealing System in Urologic Cancer Surgery" Grand Rounds in Urology 1999 vol. 1 Issue 4 pp. 10-17.

(56) References Cited

OTHER PUBLICATIONS

Craig Johnson, "Use of the LigaSure Vessel Sealing System in Bloodless Hemorrhoidectomy" Innovations That Work, Mar. 2000.
Levy et al. "Use of a New Energy-based Vessel Ligation Device During Vaginal Hysterectomy" Int'l Federation of Gynecology and Obstetrics (FIGO) World Congress 1999.
Barbara Levy, "Use of a New Vessel Ligation Device During Vaginal Hysterectomy" FIGO 2000, Washington, D.C.
E. David Crawford "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy" Sales/Product Literature 2000.
Crouch et al. "A Velocity-Dependent Model for Needle Insertion in Soft Tissue" MICCAI 2005; LNCS 3750 pp. 624-632, Dated: 2005.
McLellan et al. "Vessel Sealing for Hemostasis During Pelvic Surgery" Int'l Federation of Gynecology and Obstetrics FIGO World Congress 2000, Washington, D.C.
McLellan et al. "Vessel Sealing for Hemostasis During Gynecologic Surgery" Sales/Product Literature 1999.
Int'l Search Report EP 98944778.4 dated Oct. 31, 2000.
Int'l Search Report EP 98957771 dated Aug. 9, 2001.
Int'l Search Report EP 98957773 dated Aug. 1, 2001.
Int'l Search Report EP 98958575.7 dated Sep. 20, 2002.
Int'l Search Report EP 04013772.1 dated Apr. 1, 2005.
Int'l Search Report EP 04027314.6 dated Mar. 10, 2005.
Int'l Search Report EP 04027479.7 dated Mar. 8, 2005.
Int'l Search Report EP 04027705.5 dated Feb. 3, 2005.
Int'l Search Report EP 04709033.7 dated Dec. 8, 2010.
Int'l Search Report EP 04752343.6 dated Jul. 20, 2007.
Int'l Search Report EP 05002671.5 dated Dec. 22, 2008.
Int'l Search Report EP 05002674.9 dated Jan. 16, 2009.
Int'l Search Report EP 05013463.4 dated Oct. 7, 2005.
Int'l Search Report EP 05013894 dated Feb. 3, 2006.
Int'l Search Report EP 05013895.7 dated Oct. 21, 2005.
Int'l Search Report EP 05016399.7 dated Jan. 13, 2006.
Int'l Search Report EP 05017281.6 dated Nov. 24, 2005.
Int'l Search Report EP 05019130.3 dated Oct. 27, 2005.
Int'l Search Report EP 05019429.9 dated May 6, 2008.
Int'l Search Report EP 05020532 dated Jan. 10, 2006.
Int'l Search Report EP 05020665.5 dated Feb. 27, 2006.
Int'l Search Report EP 05020666.3 dated Feb. 27, 2006.
Int'l Search Report EP 05021197.8 dated Feb. 20, 2006.
Int'l Search Report EP 05021779.3 dated Feb. 2, 2006.
Int'l Search Report EP 05021780.1 dated Feb. 23, 2006.
Int'l Search Report EP 05021937.7 dated Jan. 23, 2006.
Int'l Search Report—extended—EP 05021937.7 dated Mar. 15, 2006.
Int'l Search Report EP 05023017.6 dated Feb. 24, 2006.
Int'l Search Report EP 06002279.5 dated Mar. 30, 2006.
Int'l Search Report EP 06005185.1 dated May 10, 2006.
Int'l Search Report EP 06006716.2 dated Aug. 4, 2006.
Int'l Search Report EP 06008515.6 dated Jan. 8, 2009.
Int'l Search Report EP 06008779.8 dated Jul. 13, 2006.
Int'l Search Report EP 06014461.5 dated Oct. 31, 2006.
Int'l Search Report EP 06020574.7 dated Oct. 2, 2007.
Int'l Search Report EP 06020583.8 dated Feb. 7, 2007.
Int'l Search Report EP 06020584.6 dated Feb. 1, 2007.
Int'l Search Report EP 06020756.0 dated Feb. 16, 2007.
Int'l Search Report EP 06 024122.1 dated Apr. 16, 2007.
Int'l Search Report EP 06024123.9 dated Mar. 6, 2007.
Int'l Search Report EP 07 001480.8 dated Apr. 19, 2007.
Int'l Search Report EP 07 001488.1 dated Jun. 5, 2007.
Int'l Search Report EP 07 004429.2 dated Nov. 2, 2010.
Int'l Search Report EP 07 009026.1 dated Oct. 8, 2007.
Int'l Search Report Extended—EP 07 009029.5 dated Jul. 20, 2007.
Int'l Search Report EP 07 009321.6 dated Aug. 28, 2007.
Int'l Search Report EP 07 010672.9 dated Oct. 16, 2007.
Int'l Search Report EP 07 013779.9 dated Oct. 26, 2007.
Int'l Search Report EP 07 014016 dated Jan. 28, 2008.
Int'l Search Report EP 07 015191.5 dated Jan. 23, 2008.
Int'l Search Report EP 07 015601.3 dated Jan. 4, 2008.
Int'l Search Report EP 07 016911 dated May 28, 2010.
Int'l Search Report EP 07 016911.5 extended dated Mar. 2, 2011.
Int'l Search Report EP 07 020283.3 dated Feb. 5, 2008.
Int'l Search Report EP 07 021646.0 dated Mar. 20, 2008.
Int'l Search Report EP 07 021646.0 dated Jul. 9, 2008.
Int'l Search Report EP 07 021647.8 dated May 2, 2008.
Int'l Search Report EP 08 002692.5 dated Dec. 12, 2008.
Int'l Search Report EP 08 004655.0 dated Jun. 24, 2008.
Int'l Search Report EP 08 006732.5 dated Jul. 29, 2008.
Int'l Search Report EP 08 006917.2 dated Jul. 3, 2008.
Int'l Search Report EP 08 016539.2 dated Jan. 8, 2009.
Int'l Search Report EP 08 020807.7 dated Apr. 24, 2009.
Int'l Search Report EP 09 003677.3 dated May 4, 2009.
Int'l Search Report EP 09 003813.4 dated Aug. 3, 2009.
Int'l Search Report EP 09 004491.8 dated Sep. 9, 2009.
Int'l Search Report EP 09 005051.9 dated Jul. 6, 2009.
Int'l Search Report EP 09 005575.7 dated Sep. 9, 2009.
Int'l Search Report EP 09 010521.4 dated Dec. 16, 2009.
Int'l Search Report EP 09 011745.8 dated Jan. 5, 2010.
Int'l Search Report EP 09 012629.3 dated Dec. 8, 2009.
Int'l Search Report EP 09 012687.1 dated Dec. 23, 2009.
Int'l Search Report EP 09 012688.9 dated Dec. 28, 2009.
Int'l Search Report EP 09 152267.2 dated Jun. 15, 2009.
Int'l Search Report Ep 09 152898.4 dated Jun. 10, 2009.
Int'l Search Report EP 09 154850.3 dated Jul. 20, 2009.
Int'l Search Report EP 09 160476.9 dated Aug. 4, 2009.
Int'l Search Report EP 09 164903.8 dated Aug. 21, 2009.
Int'l Search Report EP 09 165753.6 dated Nov. 11, 2009.
Int'l Search Report EP 09 168153.6 dated Jan. 14, 2010.
Int'l Search Report EP 09 168810.1 dated Feb. 2, 2010.
Int'l Search Report EP 09 172749.5 dated Dec. 4, 2009.
Int'l Search Report EP 10 000259.1 dated Jun. 30, 2010.
Int'l Search Report EP 10 011750.6 dated Feb. 1, 2011.
Int'l Search Report EP 10 157500.9 dated Jul. 30, 2010.
Int'l Search Report EP 10 159205.3 dated Jul. 7, 2010.
Int'l Search Report EP 10 160870.1 dated Aug. 9, 2010.
Int'l Search Report EP 10 161596.1 dated Jul. 28, 2010.
Int'l Search Report EP 10 167655.9 dated Aug. 31, 2011.
Int'l Search Report EP 10 168705.1 dated Oct. 4, 2010.
Int'l Search Report EP 10 169647.4 dated Oct. 29, 2010.
Int'l Search Report EP 10 172005.0 dated Sep. 30, 2010.
Int'l Search Report EP 10 175956.1 dated Nov. 12, 2010.
Int'l Search Report EP 10 181034.9 dated Jan. 26, 2011.
Int'l Search Report EP 10 181575.1 dated Apr. 5, 2011.
Int'l Search Report EP 10 181969.6 dated Feb. 4, 2011.
Int'l Search Report EP 10 182019 dated Aug. 4, 2011.
Int'l Search Report EP 10 182022.3 dated Mar. 11, 2011.
Int'l Search Report EP 10 185386.9 dated Jan. 10, 2011.
Int'l Search Report EP 10 185405.7 dated Jan. 5, 2011.
Int'l Search Report EP 10 186527.7 dated Jun. 17, 2011.
Int'l Search Report EP 10 189206.5 dated Mar. 17, 2011.
Int'l Search Report EP 10 191320.0 dated Feb. 15, 2011.
Int'l Search Report EP 11 151509.4 dated Jun. 6, 2011.
Int'l Search Report EP 11 152220.7 dated May 19, 2011.
Int'l Search Report EP 11 152360.1 dated Jun. 6, 2011.
Int'l Search Report EP 11 159771.2 dated May 28, 2010.
Int'l Search Report EP 11 161117.4 dated Jun. 30, 2011.
Int'l Search Report EP 11 161118.2 dated Oct. 12, 2011.
Int'l Search Report EP 11 164274.0 dated Aug. 3, 2011.
Int'l Search Report EP 11 164275.7 dated Aug. 25, 2011.
Int'l Search Report EP 11 167437.0 dated Aug. 8, 2011.
Int'l Search Report EP 11 168458.5 dated Jul. 29, 2011.
Int'l Search Report EP 11 173008.1 dated Nov. 4, 2011.
Int'l Search Report EP 11 179514 dated Nov. 4, 2011.
Int'l Search Report EP 11 180182.5 dated Nov. 15, 2011.
Int'l Search Report PCT/US98/18640 dated Jan. 29, 1999.
Int'l Search Report PCT/US98/23950 dated Jan. 14, 1999.
Int'l Search Report PCT/US98/24281 dated Feb. 22, 1999.
Int'l Search Report PCT/US99/24869 dated Feb. 3, 2000.
Int'l Search Report PCT/US01/11218 dated Aug. 14, 2001.

(56) References Cited

OTHER PUBLICATIONS

Int'l Search Report PCT/US01/11224 dated Nov. 13, 2001.
Int'l Search Report PCT/US01/11340 dated Aug. 16, 2001.
Int'l Search Report PCT/US01/11420 dated Oct. 16, 2001.
Int'l Search Report PCT/US02/01890 dated Jul. 25, 2002.
Int'l Search Report PCT/US02/11100 dated Jul. 16, 2002.
Int'l Search Report PCT/US03/08146 dated Aug. 8, 2003.
Int'l Search Report PCT/US03/18674 dated Sep. 18, 2003.
Int'l Search Report PCT/US03/18676 dated Sep. 19, 2003.
Int'l Search Report PCT/US03/28534 dated Dec. 19, 2003.
Int'l Search Report PCT/US03/28539 dated Jan. 6, 2004.
Int'l Search Report PCT/US04/03436 dated Mar. 3, 2005.
Int'l Search Report PCT/US04/13273 dated Dec. 15, 2004.
Int'l Search Report PCT/US04/15311 dated Jan. 12, 2005.
Int'l Search Report PCT/US07/021438 dated Apr. 1, 2008.
Int'l Search Report PCT/US07/021440 dated Apr. 8, 2008.
Int'l Search Report PCT/US08/52460 dated Apr. 24, 2008.
Int'l Search Report PCT/US08/61498 dated Sep. 22, 2008.
Int'l Search Report PCT/US09/032690 dated Jun. 16, 2009.

* cited by examiner

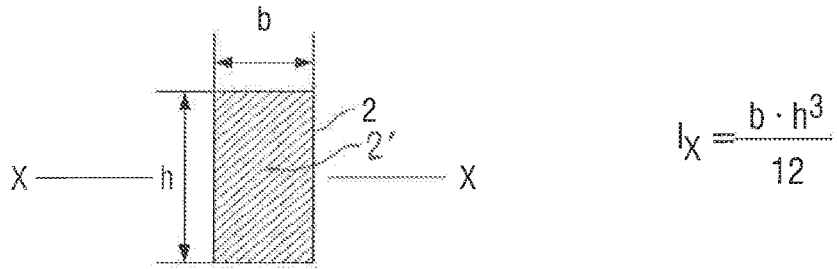

FIG. 1A

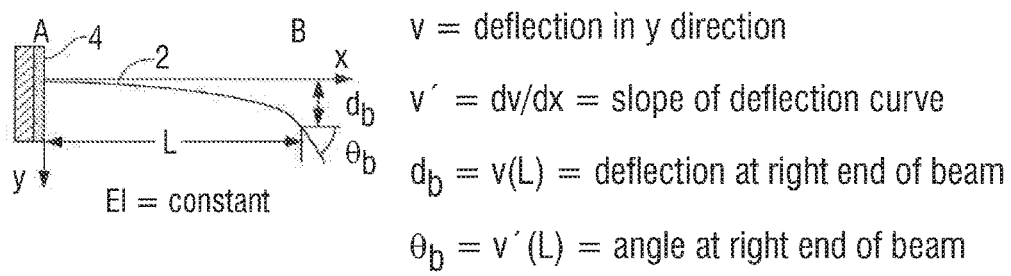

v = deflection in y direction
v′ = dv/dx = slope of deflection curve
$d_b$ = v(L) = deflection at right end of beam
$\theta_b$ = v′(L) = angle at right end of beam

FIG. 1B

| | $0 \leq X \leq A$ | $A \leq X \leq L$ | |
|---|---|---|---|
| | $v = \dfrac{Px^2}{6EI}(3a - x)$ | $v = \dfrac{Pa^2}{6EI}(3x - a)$ | $\delta_b = \dfrac{Pa^2}{6EI}(3L - a)$ |
| | $v' = \dfrac{Px}{2EI}(2a - x)$ | $v' = \dfrac{Pa^2}{6EI}$ | $\theta_b = \dfrac{Pa^2}{2EI}$ |

FIG. 1C

| | | | |
|---|---|---|---|
| | $v = \dfrac{M_0 x^2}{2EI}$ | $v = \dfrac{M_0 a}{2EI}(2x - a)$ | $\delta_b = \dfrac{M_0 a}{6EI}(2L - a)$ |
| | $v' = \dfrac{M_0 x}{EI}$ | $v' = \dfrac{M_0 a}{EI}$ | $\theta_b = \dfrac{M_0 a}{EI}$ |

FIG. 1D

IN VIVO ATTACHABLE AND DETACHABLE END EFFECTOR ASSEMBLY AND LAPAROSCOPIC SURGICAL INSTRUMENT AND METHODS THEREFOR

CROSS-REFERENCE TO RELATED APPLICATIONS

This application is a continuation of U.S. application Ser. No. 13/415,639, filed on Mar. 8, 2012, now U.S. Pat. No. 9,028,493, which is a continuation of U.S. application Ser. No. 12/562,281, filed on Sep. 18, 2009, now U.S. Pat. No. 8,133,254, the entire contents of each of which is incorporated by reference herein.

BACKGROUND

1. Technical Field

The present disclosure relates to endoscopic or laparoscopic surgery and more particularly to end effector assemblies for surgical instruments used therein.

2. Description of the Related Art

The trend in surgical procedures is to reduce the invasiveness of the procedure by reducing the size of the surgical incision. More and more frequently, the surgical incision is performed in the navel of the patient. For a laparoscopic surgical instrument, the outer shaft diameter is determined by the inner diameter of the ports (cannulae) with which the instrument will be used. As port size decreases to accommodate the reduced size of the surgical incision, the diameter/cross-sectional area of the end effectors of the surgical instrument must be reduced while the length of the end effectors must also be reduced to provide greater rigidity to reduce the susceptibility of the end effectors to deflection.

The resulting rigidity of the end effectors of the instrument thereby necessitates tight dimensional tolerances and a corresponding increase in material and manufacturing costs to provide the necessary rigidity.

SUMMARY

To advance the state of the art of surgery, the present disclosure relates to a method of performing surgery that includes the steps of providing a forceps having a housing including a shaft that extends therefrom and at least one handle moveable relative to the housing and providing an end effector assembly configured to selectively engage a distal end of the shaft. The method also includes the steps of inserting the forceps through a first opening formed in a body; inserting the end effector assembly through a second opening formed in the body; engaging the end effector assembly with the distal end of the shaft in vivo; and actuating the end effector assembly by moving the handle relative to the housing.

The method may include the step of providing a coupling at the distal end of the shaft, and may further include the step of engaging, via the coupling, the distal end of the shaft with the end effector assembly.

BRIEF DESCRIPTION OF THE DRAWINGS

Various embodiments of the present disclosure are described herein with reference to the drawings wherein:

FIG. 1A illustrates a beam having a rectangular cross-section and the corresponding equation and dimensions to calculate the moment of inertia of the beam around a particular axis;

FIG. 1B illustrates a cantilevered beam and the corresponding mathematical factors related to calculating the deflection of the beam along the length of the beam with respect to the anchor point;

FIG. 1C illustrates the cantilevered beam of FIG. 1B and the equations to calculate the deflection of the beam under a load as a function of the distance along the length of the beam with respect to the anchor point;

FIG. 1D illustrates the cantilevered beam of FIG. 1B and the equations to calculate the deflection of the beam under a bending moment as a function of the distance along the length of the beam with respect to the anchor point;

DETAILED DESCRIPTION

Figure 2:
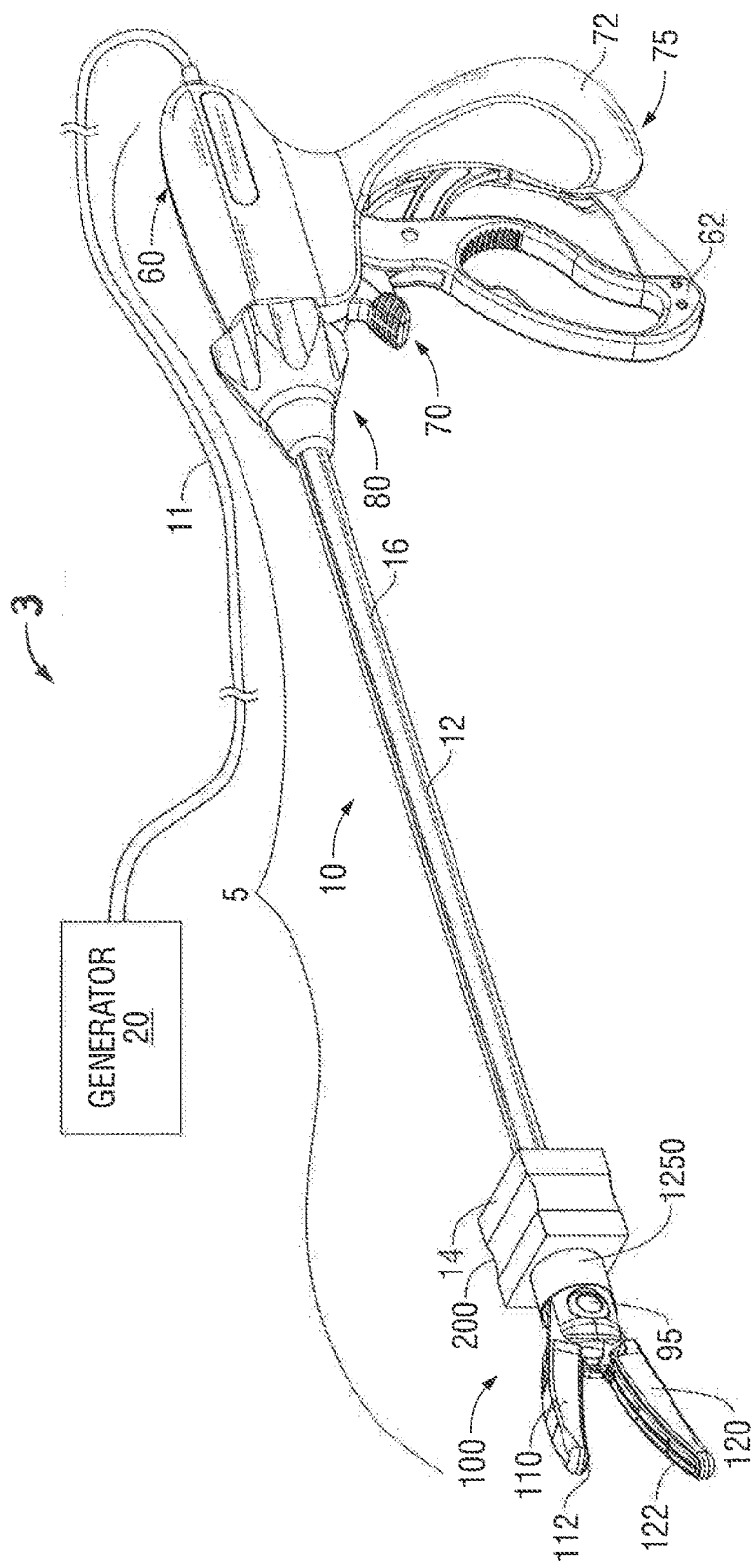
FIG. 2 is a left, perspective view of an endoscopic bipolar forceps showing a housing, a shaft and an in vivo detachable end effector assembly according to one embodiment of the present disclosure.

Various embodiments of the present disclosure are described hereinbelow with reference to the accompanying drawings. Well-known functions or constructions are not described in detail to avoid obscuring the present disclosure in unnecessary detail.

The present disclosure relates to a laparoscopic surgical instrument having a mating joint to enable attachment and detachment of a detachable end effector. The detachable end effector may be introduced into the abdominal cavity through a surgical incision such as at the navel while the laparoscopic surgical instrument is introduced, without the detachable end effector, into the abdominal cavity through another surgical incision. Alternatively, the detachable end effector may be introduced through a natural orifice such as the anal canal, while the laparoscopic surgical instrument is introduced, without the detachable end effector, through a surgical incision in the abdominal cavity.

The detachable end effector may be introduced by a second instrument, such as a grasper, which is used to attach or connect the detachable end effector to the mating joint of the instrument.

As compared to conventional laparoscopic surgical instruments, since the detachable end effector is introduced through a natural orifice of the patient, the length and the diameter of the detachable end effector of the laparoscopic surgical instrument according to the embodiments of the present disclosure may be increased.

Removal of the diameter and length constraints of the end effectors of the prior art generally allows for looser tolerances and more cost effective end effector fabrication processes. As the diameter is a significant factor in determining the necessary rigidity of the end effector assembly, a larger-diameter end effector assembly can be a longer end effector assembly because the end effector assembly will be less susceptible to deflection and thus provide a more uniform distribution of sealing pressure to the tissue.

As is well-known in the art, deflection of a cantilevered beam, which can approximate the deflection of the end effector assembly with respect to the shaft of the endoscopic instrument, is directly proportional to the distance of the applied load from an anchor point, in this case, the joint between the end effector assembly and the shaft, and inversely proportional to Young's modulus of elasticity E and the moment of inertia I of the end effector assembly, as illustrated in FIGS. 1A-1D. For an assumed rectangular cross-section $2'$ of the beam 2 as illustrated in FIG. 1A, since the moment of inertia $I_x$ around the x-axis is proportional to the width b times the cube of the height h, i.e., $h^3$, it can be seen that an increase in height h, while b remains constant, significantly increases the moment of inertia $I_x$. As can then be seen from FIGS. 1B-1C, if the beam 2 is assumed to be a cantilevered beam anchored at anchor point 4, representing the distal end of a shaft of an endoscopic instrument, the deflection v in the y-direction is directly proportional to the applied load P and the cube of the distance a from the anchor point 4, i.e., $a^3$. Since the load P and the cube of the distance a are independent of the moment of inertia $I_x$, it can then be understood that any increase in moment of inertia $I_x$ (while the other factors remain the same) will reduce the deflection v. FIG. 1D simply illustrates the same effect if one assumes a bending moment $M_0$ around anchor point 4 instead of load P.

Following completion of the surgical procedure, the detachable end effector having an enlarged moment of inertia and rigidity is detached from the mating joint via the second instrument, which may again be introduced through the natural orifice and used to withdraw the detachable end effector from the abdominal cavity while the laparoscopic surgical instrument is withdrawn through the surgical incision.

In the drawings and in the descriptions which follow, the term "proximal", as is traditional, will refer to the end of the forceps 10 which is closer to the user, while the term "distal" will refer to the end which is further from the user. It should be noted that with respect to the end effector assembly 100, reference to proximal end and distal end will be with respect to configuration of the end effector assembly 100 following attachment to the distal end 14 of the shaft 12 and corresponding actual use via the endoscopic bipolar forceps 10 during the surgical procedure, as opposed to the position of the end effector assembly 100 during the attachment process.

Referring now to FIG. 2, a tissue sealing system 3 having a combination forceps and in vivo detachable end effector assembly 5 according to the present disclosure is shown. The combination forceps and in vivo detachable end effector assembly 5 includes a forceps 10 coupled to a generator 20. Upon attachment and engagement of end effector assembly 100, as described in more detail below, the combination forceps and in vivo detachable end effector assembly 5 is adapted to seal tissue using electrosurgical energy. The generator 20 may be configured to output various types of electrosurgical energy (e.g., from about 300 MHz to about 10,000 MHz).

The forceps 10 is coupled to the generator 20 via a cable 11 adapted to transmit energy and control signals therebetween. Various embodiments of the forceps 10 utilizing the aforementioned types of energy are discussed in more detail below.

As indicated, the forceps 10 is configured to support an in vivo detachable end effector assembly 100. Forceps 10 typically includes various conventional features (e.g., a housing 60, a handle assembly 75, a rotating assembly 80, a trigger assembly 70) which enable forceps 10 and detachable end effector assembly 100 to mutually cooperate to grasp, seal and, if warranted, divide tissue. Forceps 10 generally includes housing 60 and handle assembly 75, which includes moveable handle 62 and handle 72 that is integral with housing 60. Handle 62 is moveable relative to handle 72 to actuate detachable end effector assembly 100 to grasp and treat tissue. Forceps 10 also includes a shaft 12 that has distal end 14 that mechanically engages detachable end effector assembly 100 and proximal end 16 that mechanically engages housing 60 proximate rotating assembly 80 disposed at the distal end of housing 60. Rotating assembly 80 is mechanically associated with shaft 12. Movement of rotating assembly 80 imparts similar rotational movement to shaft 12 which, in turn, rotates detachable end effector assembly 100.

Figure 3A:
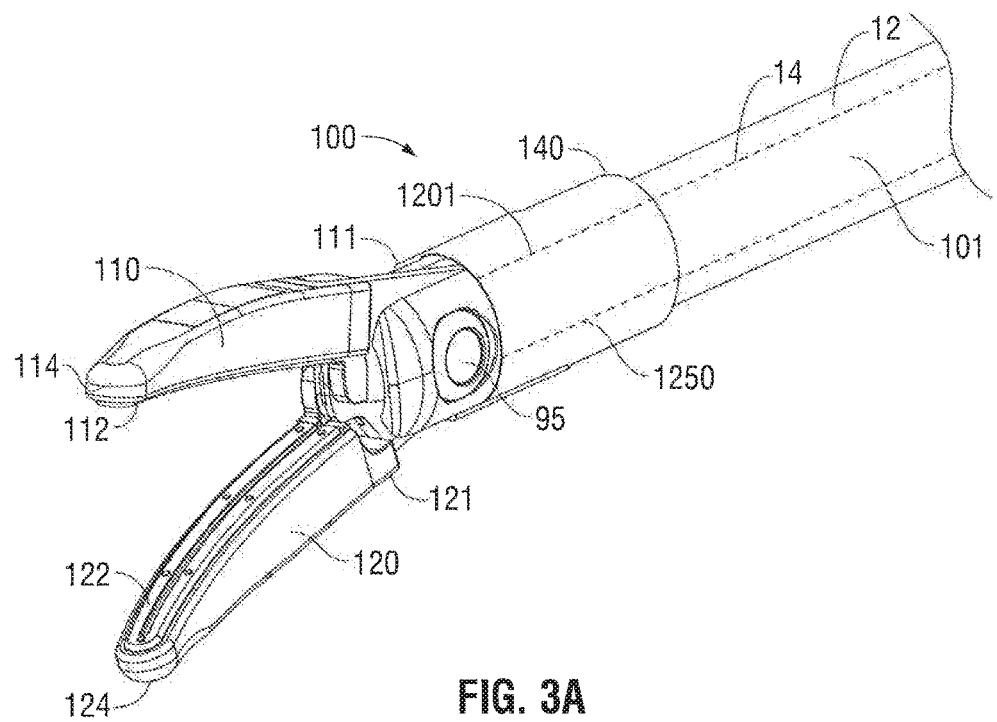
FIG. 3A is an enlarged, left, perspective view of the end effector assembly and shaft of FIG. 1 in which the in vivo detachable end effector assembly is in an open position.
Figure 3B:
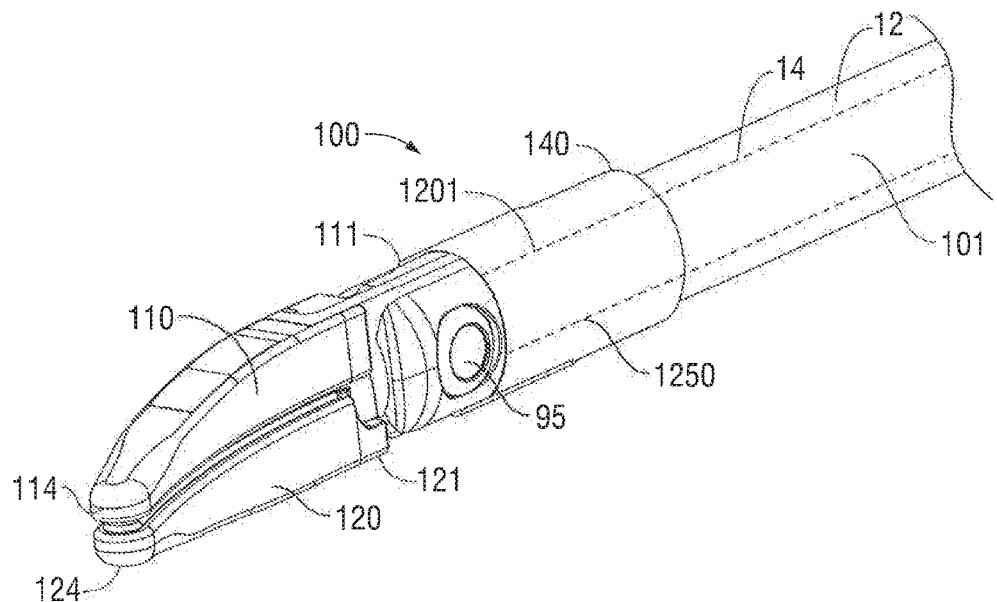
FIG. 3B is a an enlarged, left, perspective view of the end effector assembly and shaft of FIG. 1 in which the in vivo detachable end effector assembly is in a closed position.
Figure 4:
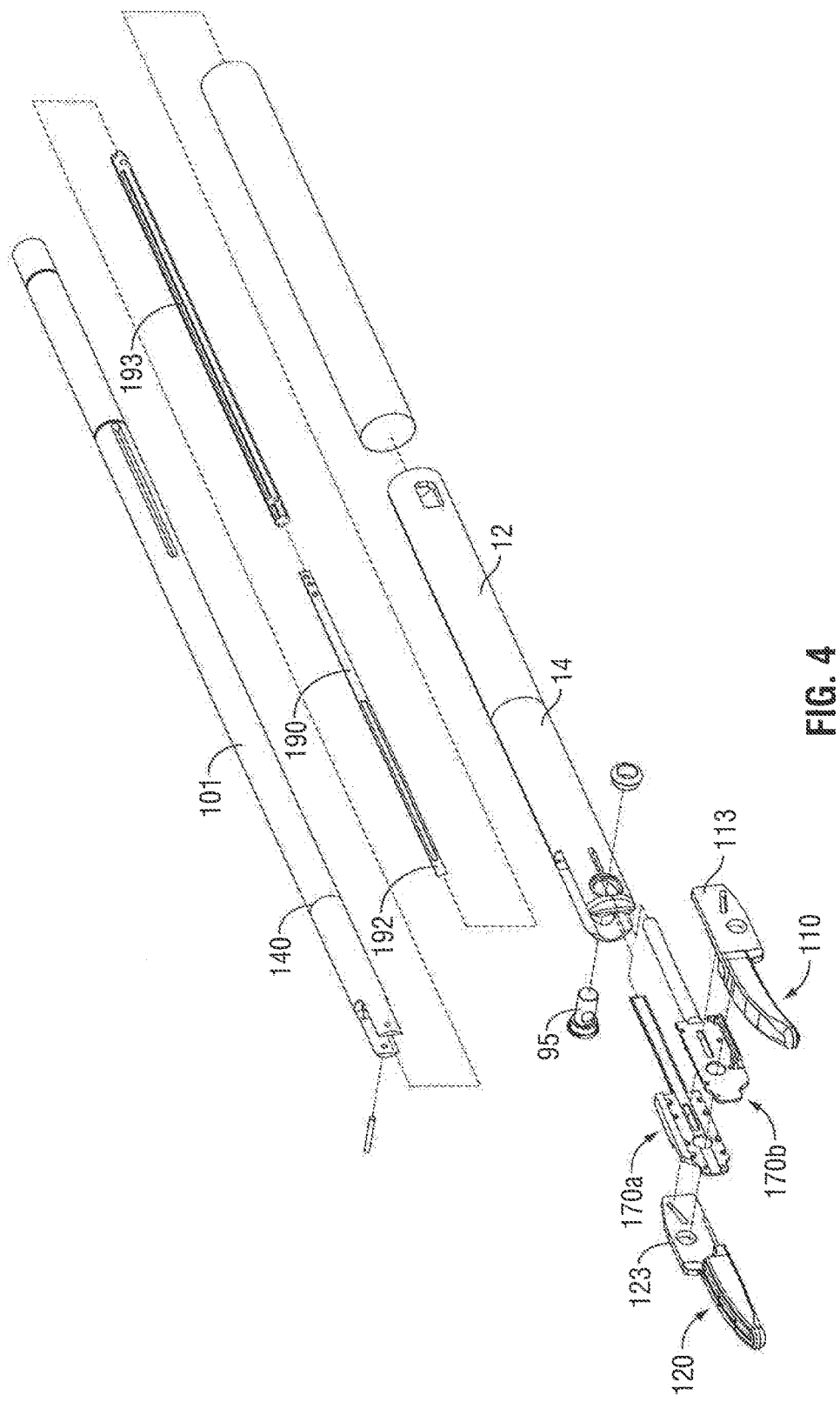
FIG. 4 is a left, perspective, exploded view of the shaft and push rod of the in vivo detachable end effector assembly.
Figure 5:
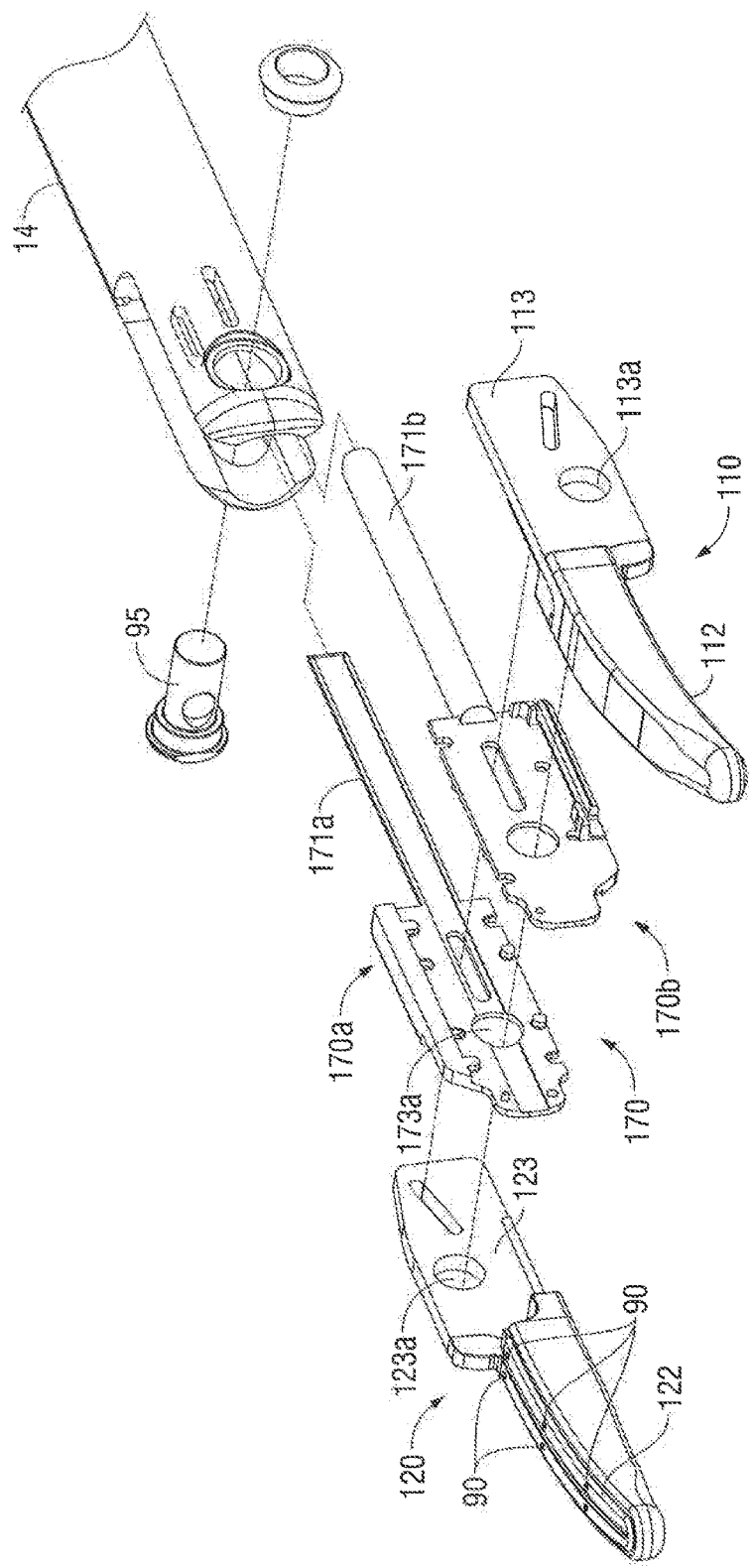
FIG. 5 is a detailed, left, perspective, exploded view of the jaw members of the in vivo detachable end effector assembly.

Referring also to FIGS. 3A-3B, detachable end effector assembly 100 includes a proximal end 1250 comprising a shaft 1201 at proximal end 1250 that is configured to engage distal end 14 of the shaft 12 of the forceps 10 at interface joint 140. The engagement between the shaft 12 and the shaft 1201 at interface joint 140 enables the attachment and detachment of the end effector assembly 100 with the forceps 10.

Detachable end effector assembly 100 also includes two jaw members 110 and 120 having proximal ends 111, 121 and distal ends 114, 124. Jaw members 110 and 120 are pivotable about a post or pivot pin 95 and are movable from a first position wherein jaw members 110 and 120 are spaced relative to another, to a second position wherein jaw members 110 and 120 are closed and cooperate to grasp tissue therebetween. As discussed in more detail below, the detachable end effector assembly 100 may be adapted for use with various energy sources.

In the illustrated embodiment, the shaft 12 houses a pushrod 101 that is operatively coupled to the movable handle 62 such that when the handle 62 is moved relative to the handle 72 the pushrod 101 moves longitudinally, either proximally or distally within the shaft 12. The pushrod 101 may include one or more pins disposed at the distal end 16 of shaft 12. Each of the jaw members 110 and 120 includes a corresponding slot disposed at the proximal ends thereof that mechanically cooperates with the push pins in a cam-follower mechanical arrangement. Motion of the pushrod 101 causes the pins to slide within respective slots 105 to actuate the jaw members. Other ways of opening/closing the jaws 110 and 120 are contemplated such as any known combinations of mechanical or electro-mechanical arrangement of gears, cams, pulleys, springs and sleeves.

The forceps 10 may also include a trigger assembly 70 that advances a knife 190 disposed within the detachable end effector assembly 100. Once a tissue seal is formed, the user activates the trigger assembly 70 to separate the tissue along the tissue seal.

Each jaw member 110 and 120 also includes a sealing surface 112 and 122, respectively, disposed on an inner-facing surface thereof. Sealing surfaces 112 and 122 cooperate to seal tissue held therebetween upon the application of energy. Sealing surfaces 112 and 122 are connected to generator 20 that communicates energy through the tissue held therebetween.

As best seen in FIG. 2, forceps 10 also includes an electrosurgical cable 11 which connects the forceps 10 to generator 20. Cable 11 is internally divided into cable leads (not shown) which each transmit electrosurgical energy through their respective feed paths through the forceps 10 to the detachable end effector assembly 100.

As mentioned above, detachable end effector assembly 100 is attached at the distal end 14 of shaft 12 and includes a pair of opposing jaw members 110 and 120. As described above, movable handles 62 and 72 mechanically cooperate to impart movement of the jaw members 110 and 120 from an open position, wherein the jaw members 110 and 120 are disposed in spaced relation relative to one another, to a clamping or closed position wherein the jaw members 110 and 120 cooperate to grasp tissue therebetween.

As shown best in FIGS. 3A-3B, 4 and 5, the detachable end effector assembly 100 is designed as a bilateral assembly, i.e., both jaw members 110 and 120 pivot relative to one another about a pivot pin 95 disposed therethrough. The jaw members 110 and 120 are curved to facilitate manipulation of tissue and to provide better "line of sight" for accessing organs and large tissue structures. In other embodiments, the jaw members 110 and 120 may have a straight configuration.

Push rod 101, which ultimately connects to a drive assembly (not shown), is dimensioned to slidingly receive knife drive rod 193, knife 190 and posts 171a and 171b of halves 170a and 170b of knife guide 170. Push rod 101, in turn, is received within shaft 12. Upon actuation of the drive assembly, the push rod 101 reciprocates which, in turn, causes the pins to ride within slots to open and close the jaw members 110 and 120 as desired. The jaw members 110 and 120, in turn, pivot about pivot pin 95 disposed through respective pivot holes 113a and 123a disposed within flanges 113 and 123.

Jaw members 110 and 120 are electrically isolated from one another such that electrosurgical energy can be effectively transferred through the tissue to form a tissue seal. Jaw members 110 and 120 are engaged to the end of rotating shaft 12 by pivot pin 95 such that rotation of the rotating assembly 80 correspondingly rotates shaft 12 (along with push rod 101 and knife 190) which, in turn, rotates detachable end effector assembly 100 (See FIG. 2).

Figure 6:
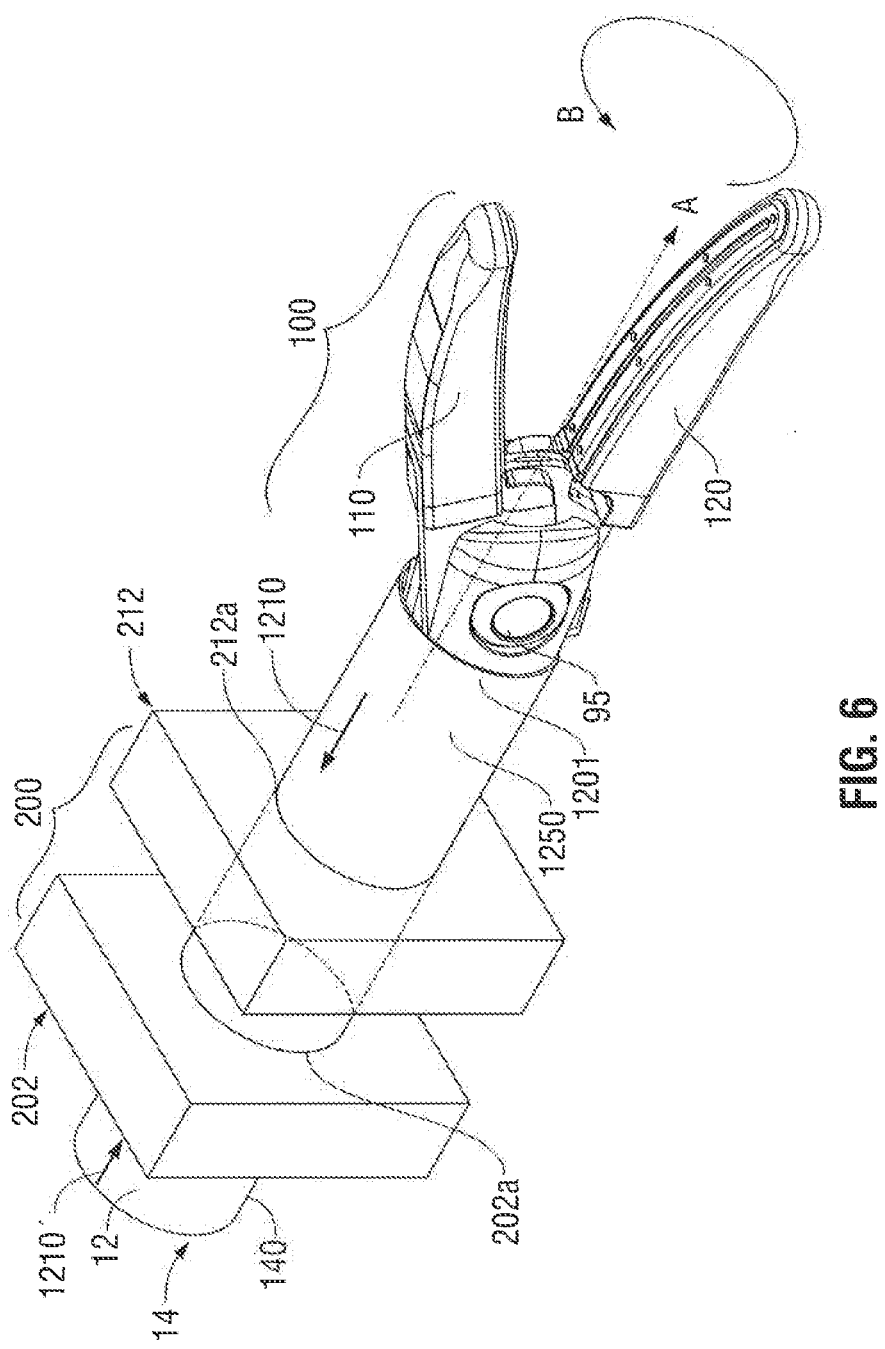
FIG. 6 is a right, perspective view of the in vivo detachable end effector assembly and the shaft generally joined by a coupling according to one embodiment of the present disclosure.

FIG. 6 illustrates the in vivo detachable end effector assembly 100 and the distal end 14 of shaft 12 of the endoscopic surgical instrument or forceps 10 that is generally joined by a coupling 200 according to one embodiment of the present disclosure. The coupling 200 has an orifice 202a at proximal end 202 and an orifice 212a at distal end 212. The orifice 202a at proximal end 202 is configured to receive the distal end 14 of shaft 12 of the endoscopic surgical instrument or forceps 10 while the orifice 212a at distal end 212 is configured to receive proximal end 1250 of the shaft 1201 of the detachable end effector assembly 100. As previously described above with respect to FIGS. 3A and 3B, detachable end effector assembly 100 includes proximal end 1250 comprising shaft 1201 at proximal end 1250 that is configured to engage distal end 14 of the shaft 12 of the forceps 10 at interface joint 140. The engagement between the shaft 12 and the shaft 1201 enables the attachment and detachment of the end effector assembly 100 with the forceps 10 during an in vivo surgical procedure. The installation of the coupling 200 during the in vivo surgical procedure thereby secures the joint 140 and enables the attachment of the end effector assembly 100 to the shaft 12 of the forceps 10. Conversely, release of the coupling 200 upon completion of activities required using the forceps 10 during the in vivo surgical procedure enables the detachment of the end effector assembly 100 from the shaft 12 of the forceps 10. To assist in the installation of the coupling 200, one or more alignment indicators, e.g., an arrow 1210 formed at an appropriate location on the shaft 1201 of the end effector assembly 100 and a corresponding arrow 1210' formed on the shaft 12 of the forceps 10, facilitate engagement of the end effector assembly 100 with the forceps 10 during an in vivo surgical procedure.

Figure 7:
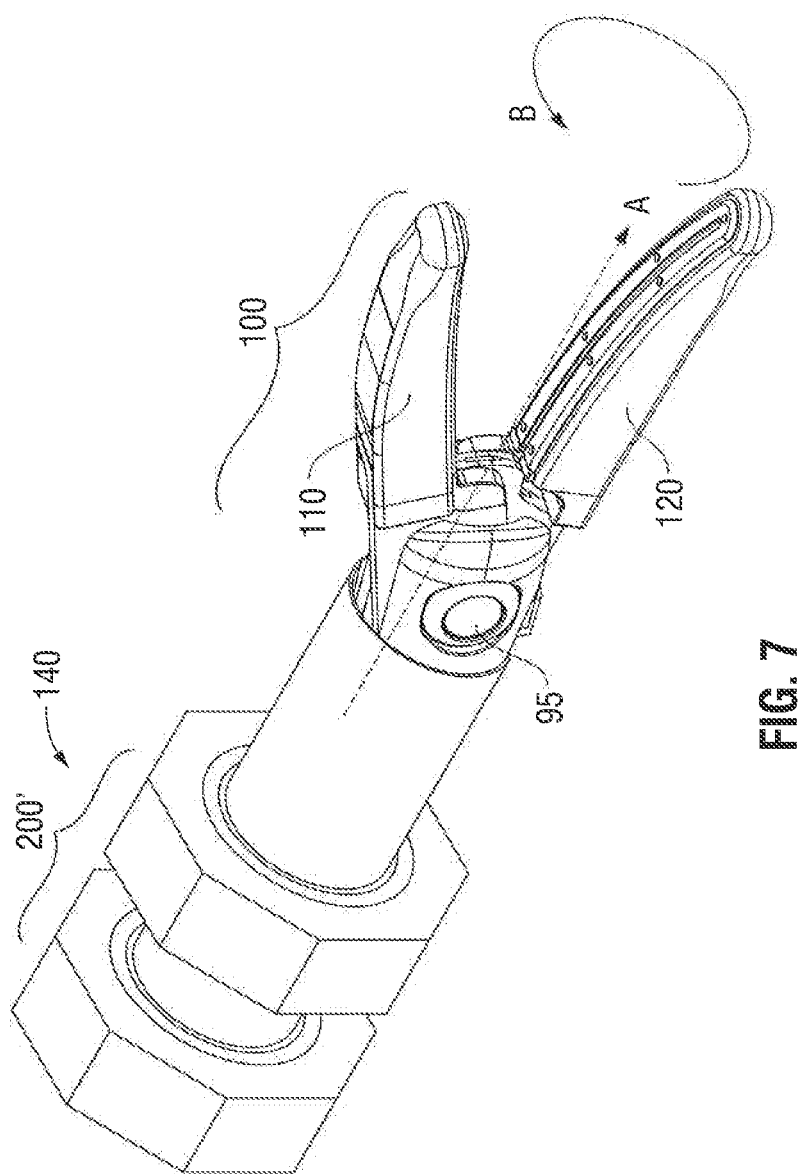
FIG. 7 is a right, perspective view of the in vivo detachable end effector assembly and the shaft joined by a compression coupling according to one embodiment of the present disclosure.

FIG. 7 illustrates the in vivo detachable end effector assembly 100 and the shaft 12 of forceps 10 joined at interface joint 140 by an example coupling, e.g., a compression coupling 200' that may have a compression fitting at one or both ends or a compression fitting at one end and another type of fitting such as a screw threaded fitting at the other end, according to one embodiment of the present disclosure. Numerous other suitable couplings may be employed to perform the joining of the end effector assembly 100 and the shaft 12, including, but not limited to, Luer lock fittings, snap-fit coupling, ball and socket fittings and the like.

The shaft 12 and the end effector assembly 100 are configured such that engagement of the end effector assembly 100 with the distal end 14 of the shaft 12 establishes electrical communication between the forceps 10 and the tissue sealing surface 112 and/or 122 of the end effector assembly 100.

As also described above previously, the distal end 14 of the shaft 12 is configured to interface with coupling 200. The coupling 200 is configured to interface with the end effector assembly 100. The end effector assembly 100 is configured to detachably engage and disengage from the distal end 14 of the shaft 12 via engagement of the end effector assembly 100 with the coupling 200.

The shaft 12 and the end effector assembly 100 are configured such that engagement of the end effector assembly 100 with the distal end 14 of the shaft 12 via the coupling 200 establishes electrical communication between the forceps 10 and the end effector assembly 100.

To accomplish the intended purpose of the combination forceps and in vivo detachable end effector assembly 5 (see FIG. 2), the end effector assembly 100 may be configured to vary the ratio between the moment of inertia of the cross-section of the end effector assembly and the moment of inertia of the cross-section of the shaft 12 depending on any particular surgical purpose.

In addition, coupling 200 may be configured to selectively engage a first end effector assembly having a cross-sectional moment of inertia value and a second end effector assembly having a cross-sectional moment of inertia value that differs from the cross-sectional moment of inertia value of the first end effector assembly. That is, the coupling may be a universal type coupling configured to selectively engage end effector assemblies of different or various sizes.

Figure 8:
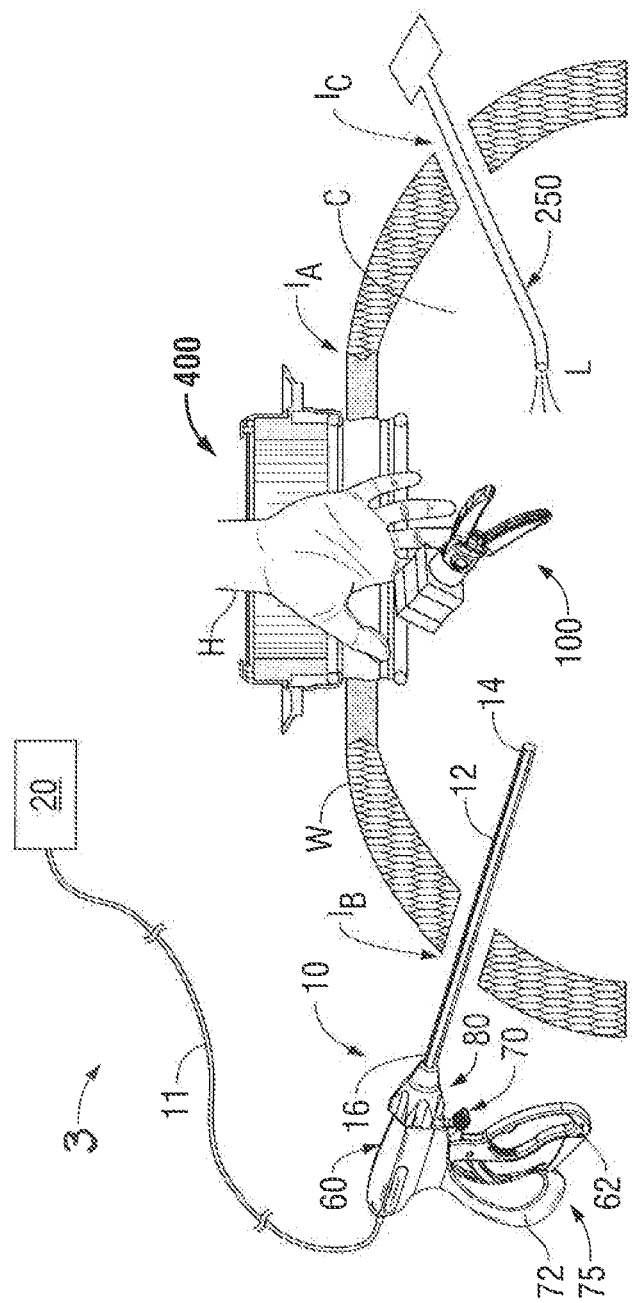
FIG. 8 is a simplified view of an abdominal cavity in a subject illustrating an in vivo method of attaching a detachable end effector assembly to an endoscopic surgical instrument during a laparoscopic procedure according to one embodiment of the present disclosure.
Figure 9:
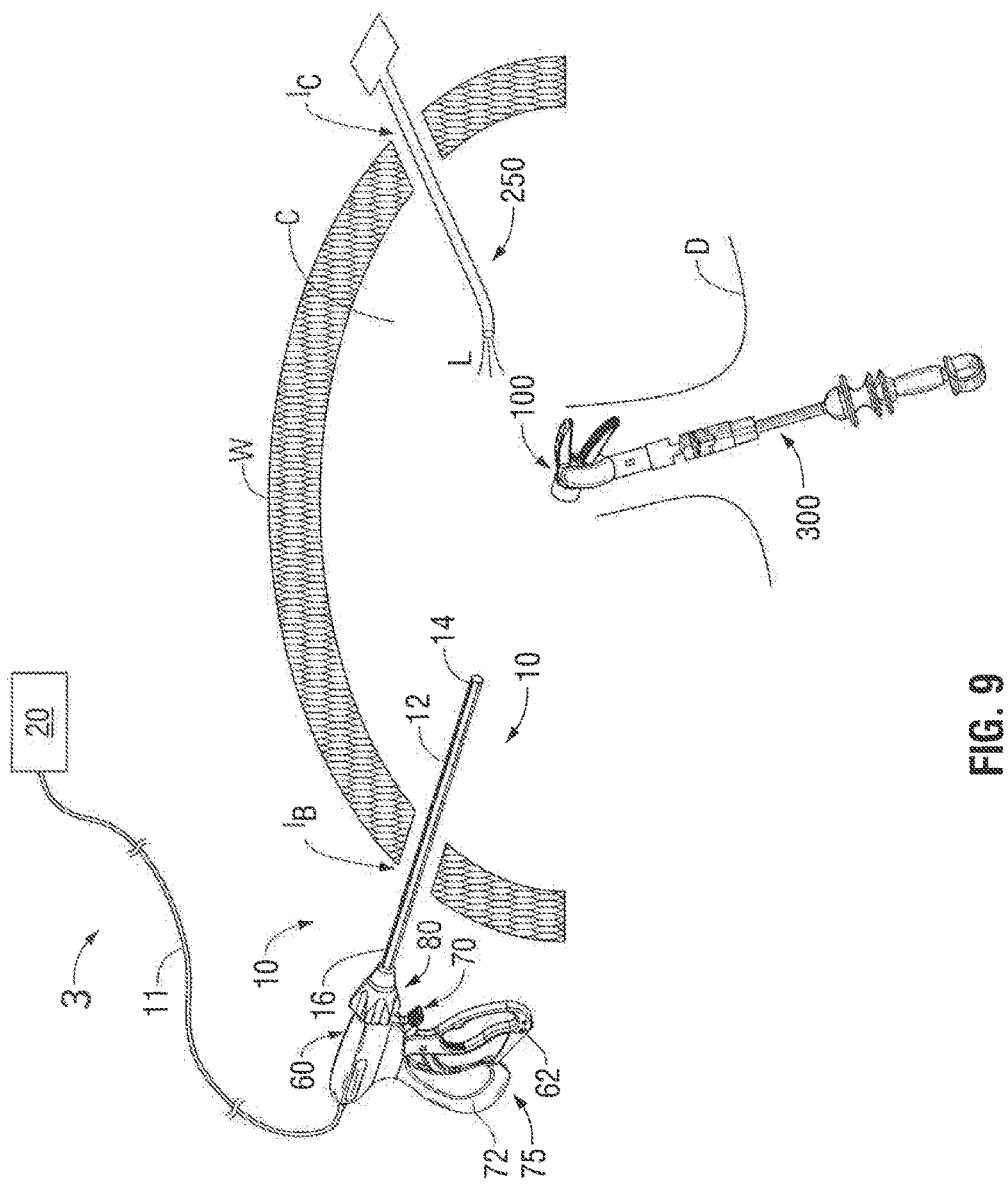
FIG. 9 is a simplified view of an abdominal cavity in a subject illustrating an in vivo method of attaching, via a grasping device, a detachable end effector assembly to an endoscopic surgical instrument during a laparoscopic procedure according to another embodiment of the present disclosure.
Figure 10:
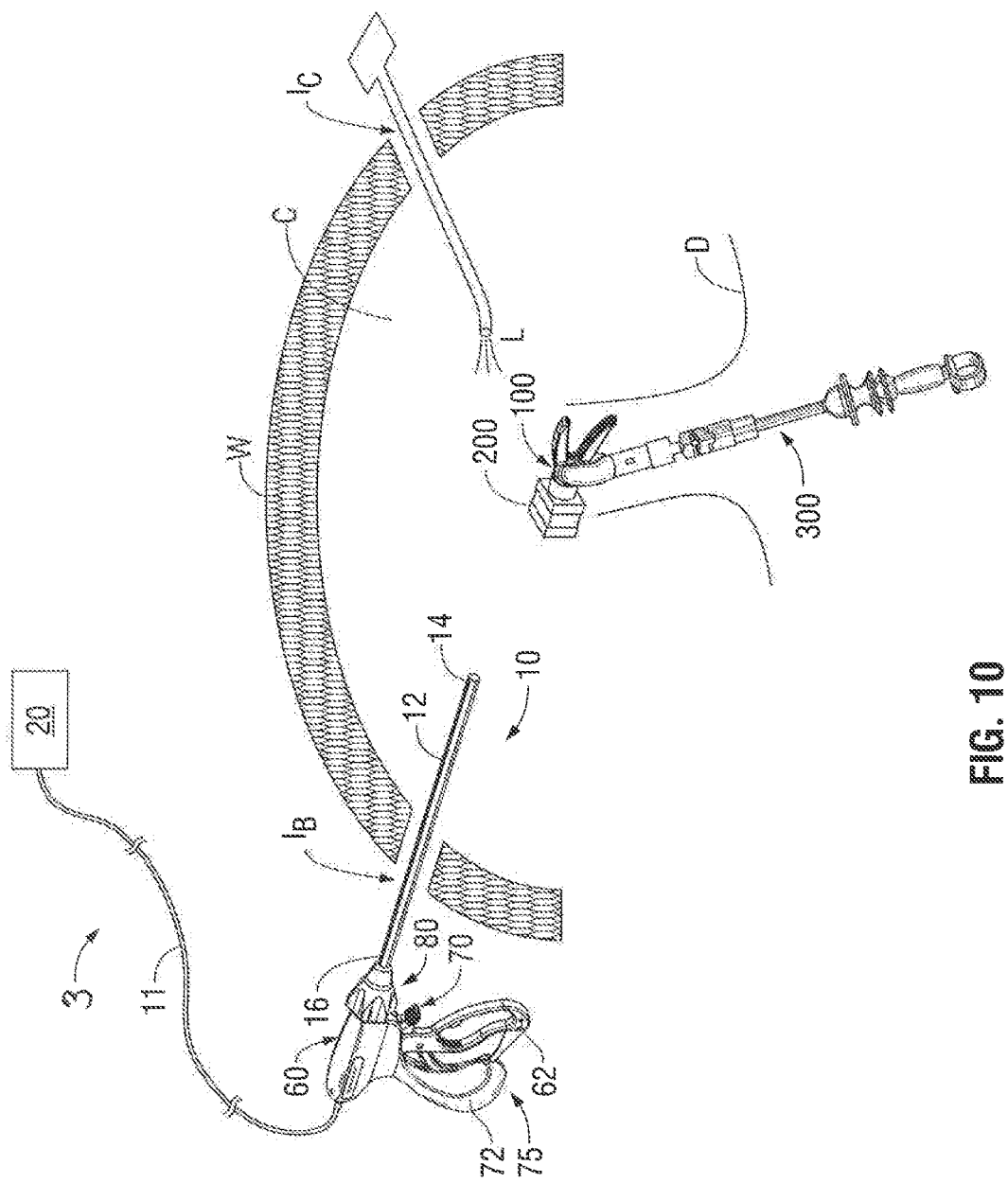
FIG. 10 is a simplified view of an abdominal cavity in a subject illustrating an in vivo method of attaching a detachable end effector assembly to an endoscopic surgical instrument during a laparoscopic procedure via a coupling that is configured to interface with the end effector assembly and the endoscopic surgical instrument according to still another embodiment of the present disclosure.

FIGS. 8-10 illustrate simplified views of portions of the in vivo method of attaching the detachable end effector assembly 100 to the forceps 10 to form the combination forceps and end effector assembly 5 (see FIG. 2) for use during the surgical procedure to seal and cut tissue.

More particularly, FIG. 8 is a simplified view of an abdominal cavity C in a subject illustrating the in vivo method of attaching detachable end effector assembly 100 to forceps 10 during a laparoscopic procedure according to one embodiment of the present disclosure. A surgical hand access apparatus 400 is shown installed within an opening or surgical incision $I_A$ in abdominal wall W located at a position such as at the navel of the subject as shown. Such a surgical hand access apparatus and the method of installation are described in commonly-owned U.S. Patent Application Publication US 2006/0229501 A1, by Jensen et al., entitled "SURGICAL HAND ACCESS APPARATUS", now U.S. Pat. No. 7,766,824 issued on Aug. 3, 2010. The hand H of a surgeon is illustrated grasping the in vivo detachable end effector assembly 100 and inserting or positioning the end effector assembly 100 through the incision $I_A$ and into the abdominal cavity C. The end effector assembly 100 is grasped and oriented in a position to facilitate attachment and engagement of the end effector assembly 100 with the forceps 10.

The forceps 10 is provided and inserted, minus the detachable end effector assembly 100, through another opening or incision $I_B$ in the body that allows the surgeon to position the distal end 14 of the shaft 12 such that upon attachment and engagement of the end effector assembly 100 to the shaft 12, the resulting combination forceps and end effector assembly 5 (see FIG. 2) is advantageously positioned to perform the desired surgical procedure.

Although not shown, the method further includes the step of engaging the end effector assembly 100 with the distal end 14 of the shaft 12. The step of engaging the end effector assembly 100 with the distal end 14 of the shaft 12 enables establishment of electrical communication between the forceps 10 and the tissue sealing surface 112 and/or 122 of jaw members 110 and/or 120 of the end effector assembly 100.

When at least one jaw member, e.g., lower jaw member 120, of the end effector assembly 100 further includes a mechanical cutting element, e.g., knife blade 190, the step of engaging the end effector assembly 100 with the distal end 14 of the shaft 12 also enables establishment of mechanical communication between the forceps 10 and the mechanical cutting element of the jaw member 120 to enable mechanical cutting of tissue.

As described above to assist in the installation of the coupling 200, the method may include providing one or more alignment indicators, e.g., arrow 1210 formed at an appropriate location on the shaft 1201 of the end effector assembly 100 and/or corresponding arrow 1210' formed on the shaft 12 of the forceps 10, to facilitate engagement of the end effector assembly 100 with the forceps 10 during an in vivo surgical procedure. The step of aligning the end effector assembly 100 with the forceps 10 may include rotating the end effector assembly 100, in the direction indicated by arrow B around longitudinal axis A of the end effector assembly 100, and also translating the end effector assembly 100 in the direction of the longitudinal axis A, as illustrated in FIGS. 6 and 7.

To further assist the surgeon in implementing the attachment and engagement of the end effector assembly 100 to the shaft 12 and in implementing the surgical procedure, an endoscopic camera 250 may be positioned and inserted through the abdominal wall W into the abdominal cavity C through another opening or incision $I_C$ in the body at an opposite side of the abdominal wall W to facilitate transmission of light L towards the end effector assembly 100 and the distal end 14 of the shaft 12 and to facilitate reception of cinematic images.

FIG. 9 is a simplified view of the abdominal cavity C in a subject illustrating an in vivo method of attaching, via a grasping device, the detachable end effector assembly 100 to the forceps 10 during a laparoscopic procedure according to another embodiment of the present disclosure. A grasping device 300, such as the endoscopic surgical device having an articulating handle assembly that is disclosed in commonly-owned U.S. patent application Ser. No. 12/193,864 by De Santis et al., filed on Aug. 19, 2008, entitled "ENDOSCOPIC SURGICAL DEVICE", published on Feb. 26, 2009 as U.S. Patent Application Publication No. US 2009/0054734 A1, the entire contents of which are hereby incorporated by reference herein, is positioned and inserted through an opening in the body such as a natural orifice D, Again, the end effector assembly 100 is grasped and oriented in a position to facilitate attachment and engagement of the end effector assembly 100 with the forceps 10.

In a similar manner as described above with respect to FIG. 8, the forceps 10 is provided and inserted, minus the detachable end effector assembly 100, through opening or incision $I_B$ in the body that allows the surgeon to position the distal end 14 of the shaft 12 such that upon attachment and engagement of the end effector assembly 100 to the shaft 12, the resulting combination forceps and end effector assembly 5 (see FIG. 2) is advantageously positioned to perform the desired surgical procedure.

Again, although not shown, the method may further include the step of engaging the end effector assembly 100 with the distal end 14 of the shaft 12. The step of engaging the end effector assembly 100 with the distal end 14 of the shaft 12 enables establishment of electrical communication between the forceps 10 and the end effector assembly 100.

In a similar manner, when at least one jaw member, e.g., lower jaw member 120, of the end effector assembly 100 further includes a mechanical cutting element, e.g., knife blade 190, the step of engaging the end effector assembly 100 with the distal end 14 of the shaft 12 also enables establishment of mechanical communication between the forceps 10 and the mechanical cutting element (knife blade 190) of the jaw member 120 to enable mechanical cutting of tissue.

FIG. 10 is a simplified view of the abdominal cavity C in a subject illustrating an alternative in viva method of attaching the detachable end effector assembly 100 to forceps 10 during a laparoscopic procedure, as compared to the in vivo method described above with respect to FIG. 9, via the coupling 200 that is configured to interface with the end effector assembly 100 and the forceps 10, according to still another embodiment of the present disclosure.

As described previously above with respect to FIGS. 6 and 7, the end effector assembly 100 and the distal end 14 of the shaft 12 of the forceps 10 are configured to interface with the coupling 200. As can be appreciated, the previous steps of implementing the method of engaging the forceps 10 with the end effector assembly 100 described above with respect to FIG. 9 are each implemented by interfacing the coupling 200 with the end effector assembly 100 and with the distal end 14 of the shaft 12.

The methods described above with respect to FIGS. 8-10 may be implemented wherein forceps 10 includes trigger assembly 70 (that includes a trigger—see FIG. 2) operably coupled to the housing 60 and the end effector assembly 100 includes a knife 192 (see FIG. 4) and the method includes the step of actuating the trigger 70 to advance the knife 192 to separate tissue disposed in the end effector assembly 100.

Additionally, the method may be implemented by providing coupling 200 configured to selectively engage a first end effector assembly having a cross-sectional moment of inertia value and a second end effector assembly having a cross-sectional moment of inertia value that differs from the cross-sectional moment of inertia value of the first end effector assembly depending on a surgical need. That is, as described previously, the coupling 200 may be a universal type coupling configured to selectively engage end effector assemblies of different or various sizes depending on the requirements for a particular surgical procedure or need.

Actuation of the handles 62 and 72 closes the jaw members 110 and 120 about tissue with a pre-determinable and consistent closure pressure to effect a tissue seal. Closure pressures for sealing large tissue structures fall within the range of about 3 kg/cm$^2$ to about 16 kg/cm$^2$.

Stop members 90 which extend from the sealing surface 122 provide a consistent and accurate gap distance "G" (not shown) between the electrically conductive sealing surfaces 112 and in the range from about 0.001 inches (about 0.0254 millimeters) to about 0.006 inches (about 0.1524 millimeters) which is also effective for sealing tissue.

After the tissue is grasped between jaw members 110 and 120, the forceps 10 is ready for selective application of electrosurgical energy and subsequent separation of the tissue. By controlling the intensity, frequency and duration of the electrosurgical energy and pressure applied to the tissue, the user can effectively seal tissue.

Referring to FIG. 2, it can be appreciated from the foregoing that the embodiments of the present disclosure may include a kit for an in vivo surgical procedure that includes forceps 10 having housing 60 including shaft 12 that extends therefrom and at least one handle 62 that is movable relative to the housing 60. The kit also includes the selectively engageable end effector assembly 100 that is configured to selectively engage the distal end 14 of the shaft 12. The kit may further include coupling 200 that is configured to facilitate engagement of the end effector assembly 100 to the forceps 10.

The state of the art of endoscopic surgery is advanced by the embodiments of the present disclosure, since the embodiments of the present disclosure enable removing the diameter and length constraints of the end effectors of the prior art to generally allow for looser tolerances and more cost effective end effector fabrication processes. As described above, the diameter is a significant factor in determining the necessary rigidity of the end effector assembly, so that a larger-diameter end effector assembly can be a longer end effector assembly because the end effector assembly will be less susceptible to deflection and thus will provide a more uniform distribution of sealing pressure to the tissue.

While several embodiments of the disclosure have been shown in the drawings and/or discussed herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A kit for an in vivo surgical procedure, comprising:
a forceps including:
    a housing having a shaft that extends therefrom, the shaft including a proximal end that is configured to operably couple to the housing and a distal end that extends therefrom; and
    a handle operably associated with the housing and selectively movable relative thereto;
    a selectively engageable end effector assembly configured to selectively engage the distal end of the shaft in vivo, wherein the shaft defines a cross-sectional moment of inertia, and wherein the selectively engageable end effector assembly defines a cross-sectional moment of inertia; and
a coupling configured to facilitate engagement and disengagement of the end effector assembly in vivo to and from the shaft, respectively, wherein the coupling is configured with a cross-sectional moment of inertia that is greater than the cross-sectional moments of inertia of both the shaft and the selectively engageable end effector assembly to yield an enlarged moment of inertia and rigidity to the forceps via the coupling.

2. The kit according to claim 1, wherein the coupling is configured to selectively engage a first end effector assembly having a cross-sectional moment of inertia value and the coupling is configured to selectively engage a replacement, second end effector assembly having a cross-sectional moment of inertia value that is the same as the cross-sectional moment of inertia value of the first end effector assembly.

3. The kit according to claim 1, wherein the coupling is configured to selectively engage a first end effector assembly having a cross-sectional moment of inertia value and the coupling is configured to selectively engage a replacement, second end effector assembly having a cross-sectional moment of inertia value that is different from the cross-sectional moment of inertia value of the first end effector assembly.

4. The kit according to claim 1, wherein the coupling is a compression coupling that includes first and second ends that are compression fittings.

5. The kit according to claim 1, wherein the coupling includes a first end that is a compression coupling and a second end that is a threaded fitting.

6. The kit according to claim 1, wherein the coupling includes first and second ends that are selected from the group consisting of Luer lock fittings, snap-fit couplings, and ball and socket fittings.

7. A surgical forceps, comprising:
a housing having a shaft that extends therefrom, the shaft including a proximal end that is configured to operably couple to the housing and a distal end that extends therefrom;
a handle operably associated with the housing and selectively movable relative thereto;
a selectively engageable end effector assembly configured to selectively engage the distal end of the shaft in vivo, wherein the shaft defines a cross-sectional moment of inertia, and wherein the selectively engageable end effector assembly defines a cross-sectional moment of inertia; and a coupling configured to facilitate engagement and disengagement of the end effector assembly in vivo to and from the shaft, respectively, wherein the coupling is configured with a cross-sectional moment of inertia that is greater than the cross-sectional moments of inertia of both the shaft and the selectively engageable end effector assembly to yield an enlarged moment of inertia and rigidity to the forceps via the coupling.

8. The surgical forceps according to claim 7, wherein the coupling is configured to selectively engage a first end effector assembly having a cross-sectional moment of inertia value and the coupling is configured to selectively engage a replacement, second end effector assembly having a cross-sectional moment of inertia value that is the same as the cross-sectional moment of inertia value of the first end effector assembly.

9. The surgical forceps according to claim 7, wherein the coupling is configured to selectively engage a first end effector assembly having a cross-sectional moment of inertia value and the coupling is configured to selectively engage a replacement, second end effector assembly having a cross-sectional moment of inertia value that is different from the cross-sectional moment of inertia value of the first end effector assembly.

10. The surgical forceps according to claim 7, wherein the coupling is a compression coupling that includes first and second ends that are compression fittings.

11. The surgical forceps according to claim 7, wherein the coupling includes a first end that is a compression coupling and a second end that is a threaded fitting.

12. The surgical forceps according to claim 1, wherein the coupling includes first and second ends that are selected from the group consisting of luer lock fittings, snap-fit couplings, and ball and socket fittings.

\* \* \* \* \*